(12) United States Patent
Haidukewych et al.

(10) Patent No.: US 12,408,956 B2
(45) Date of Patent: Sep. 9, 2025

(54) BONE PLATES, AND RELATED SYSTEMS AND METHODS

(71) Applicant: DePuy Synthes Products, Inc., Raynham, MA (US)

(72) Inventors: George John Haidukewych, Orlando, FL (US); Kenny Koay, West Chester, PA (US); Morgan Brett Smith, Downington, PA (US); Frank Anthony Liporace, Fort Worth, TX (US); Cory A. Collinge, Fort Worth, TX (US)

(73) Assignee: DePuy Synthes Products, Inc., Raynham, MA (US)

( * ) Notice: Subject to any disclaimer, the term of this patent is extended or adjusted under 35 U.S.C. 154(b) by 216 days.

(21) Appl. No.: 18/171,827

(22) Filed: Feb. 21, 2023

(65) Prior Publication Data
US 2024/0277388 A1 Aug. 22, 2024

(51) Int. Cl.
*A61B 17/72* (2006.01)
*A61B 17/80* (2006.01)

(52) U.S. Cl.
CPC ...... *A61B 17/7233* (2013.01); *A61B 17/8057* (2013.01)

(58) Field of Classification Search
CPC ..... A61B 17/72; A61B 17/7233; A61B 17/80; A61B 17/8052; A61B 17/808
USPC ........................................... 606/62, 280, 281
See application file for complete search history.

(56) References Cited

U.S. PATENT DOCUMENTS

| | | |
|---|---|---|
| 3,709,218 A | 1/1973 | Halloran |
| 8,157,803 B1 | 4/2012 | Zirkle et al. |
| 8,372,152 B2 | 2/2013 | Kirschman |
| 8,734,448 B2 | 5/2014 | Thakkar |
| 8,753,343 B2 | 6/2014 | Staeubli |
| 9,005,253 B2 | 4/2015 | Appenzeller et al. |
| 9,463,054 B2 | 10/2016 | Mueckter |
| 9,788,872 B2 | 10/2017 | Wagner et al. |
| 10,314,626 B2 | 6/2019 | Koay et al. |
| 10,548,649 B2 | 2/2020 | Sixto et al. |
| 11,589,877 B2 * | 2/2023 | Duerr .................. A61B 17/152 |

(Continued)

FOREIGN PATENT DOCUMENTS

| | | |
|---|---|---|
| EP | 2099373 B1 | 10/2014 |
| WO | 2009/068011 A2 | 6/2009 |

*Primary Examiner* — Eduardo C Robert
*Assistant Examiner* — Christina Negrellirodriguez
(74) *Attorney, Agent, or Firm* — BakerHostetler

(57) ABSTRACT

A bone plate includes first and second ends opposed along a longitudinal axis oriented along a longitudinal direction, first and second sides opposed along a lateral direction, and a bone-facing surface and an outer surface opposed along a transverse direction. The plate defines a first hole and a second hole arrangement extending from the outer to the bone-facing surface. The second hole arrangement is distal of the first hole, which is configured to receive a first fixation member, and the second hole arrangement is configured to receive at least one second fixation member for affixing with underlying bone. The plate is pivotable along an angulation range about the first hole. The second hole arrangement laterally crosses the longitudinal axis, defines the angulation range, and allows the at least one second fixation member to substantially secure the plate to the underlying bone at any angulation within the angulation range.

20 Claims, 10 Drawing Sheets

(56) References Cited

U.S. PATENT DOCUMENTS

| | | |
|---|---|---|
| 2003/0135212 A1 | 7/2003 | Y Chow |
| 2005/0273112 A1* | 12/2005 | McNamara .......... A61B 17/152 |
| | | 606/87 |
| 2006/0100623 A1 | 5/2006 | Pennig |
| 2008/0140127 A1 | 6/2008 | Vasta et al. |
| 2009/0177240 A1 | 7/2009 | Perez |
| 2010/0256685 A1 | 10/2010 | Plecko et al. |
| 2011/0190769 A1 | 8/2011 | Haininger |
| 2017/0056081 A1 | 3/2017 | Langdale et al. |
| 2018/0256220 A1 | 9/2018 | Koay et al. |
| 2018/0256221 A1 | 9/2018 | Koay et al. |
| 2020/0107867 A1 | 4/2020 | Bogle |
| 2021/0059727 A1 | 3/2021 | Fatone et al. |
| 2022/0117639 A1 | 4/2022 | Gabelberger et al. |

* cited by examiner

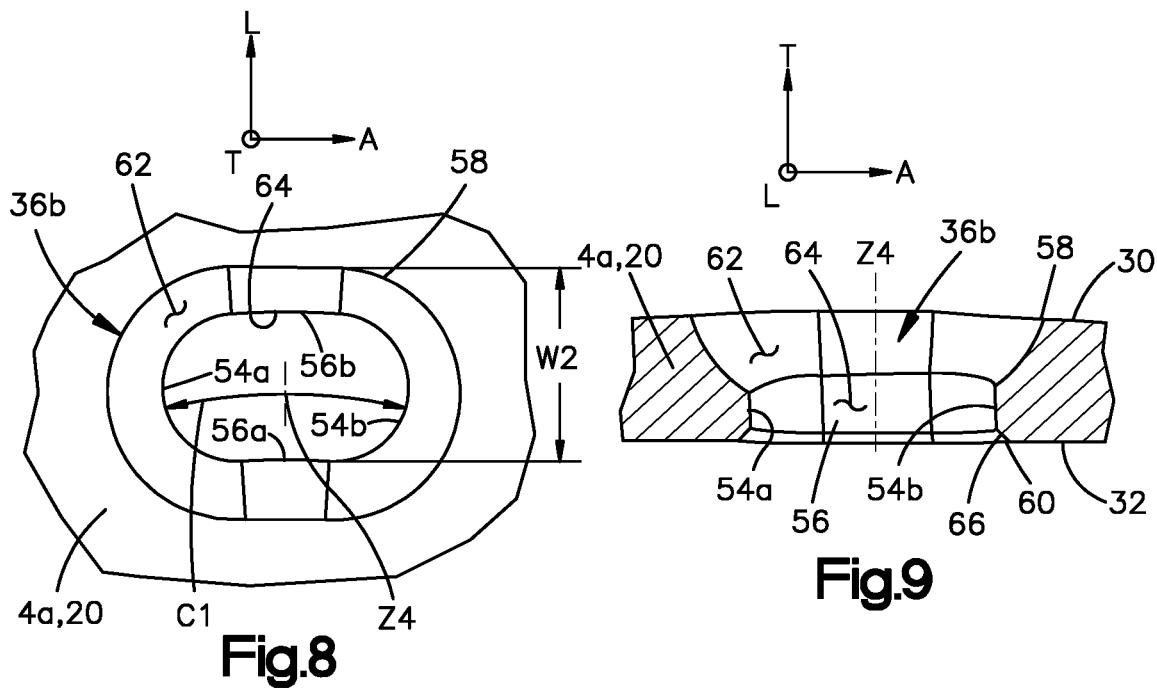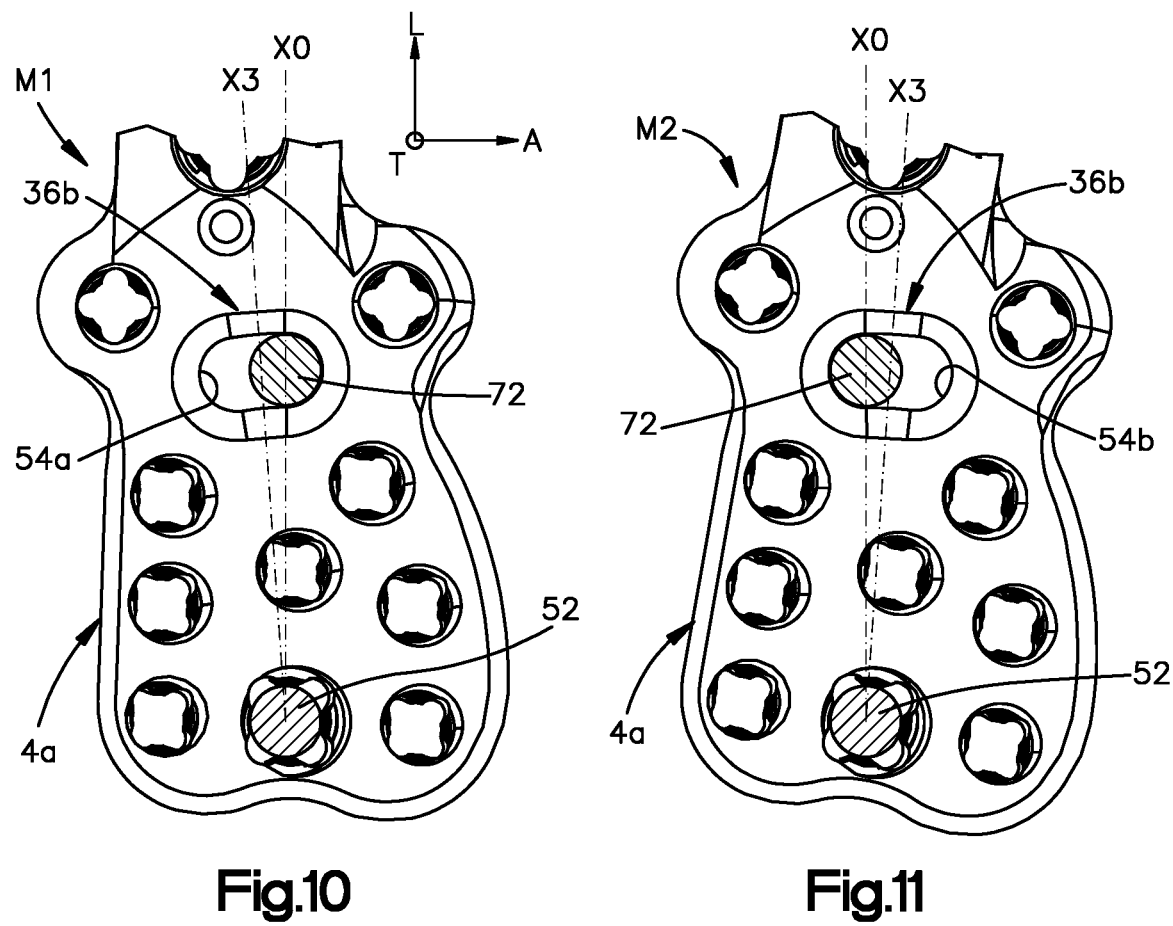

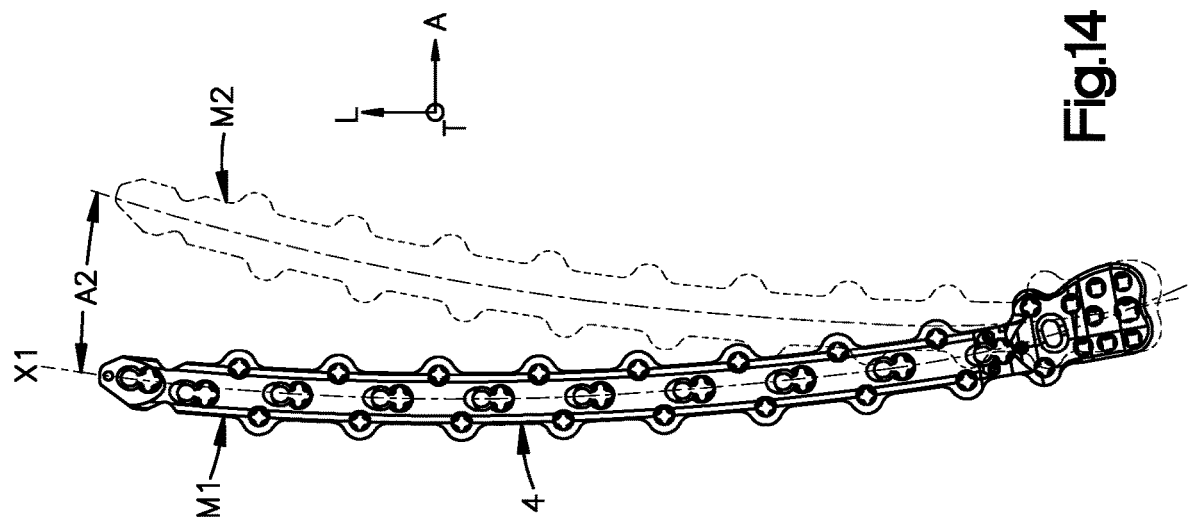
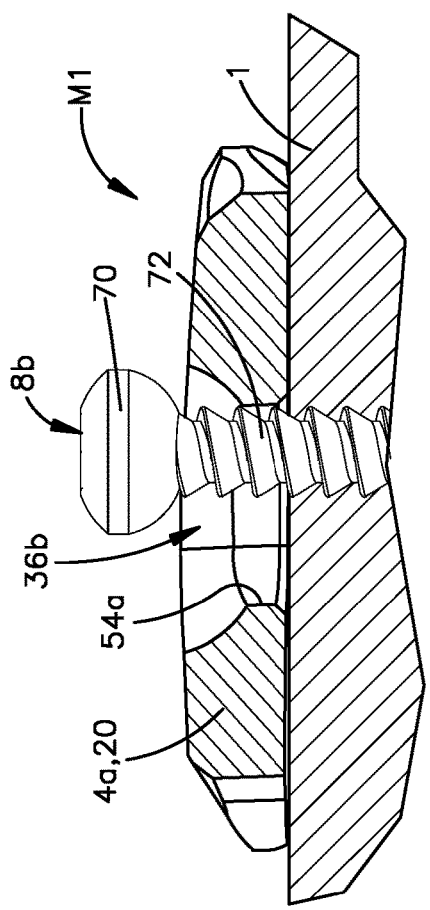
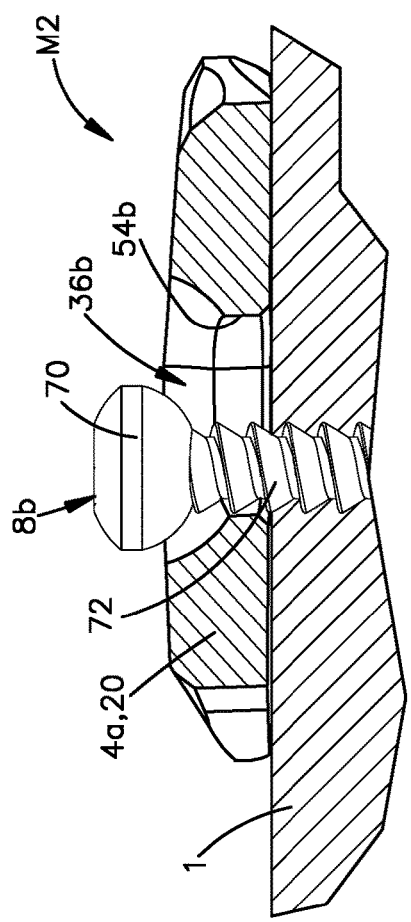

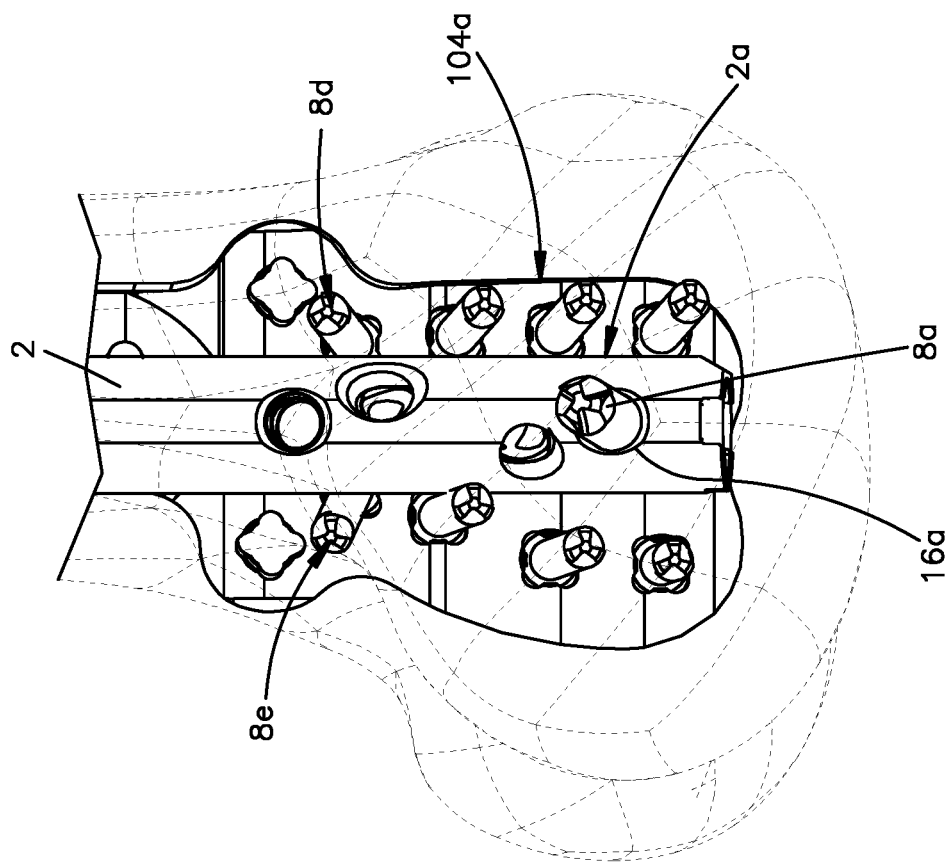
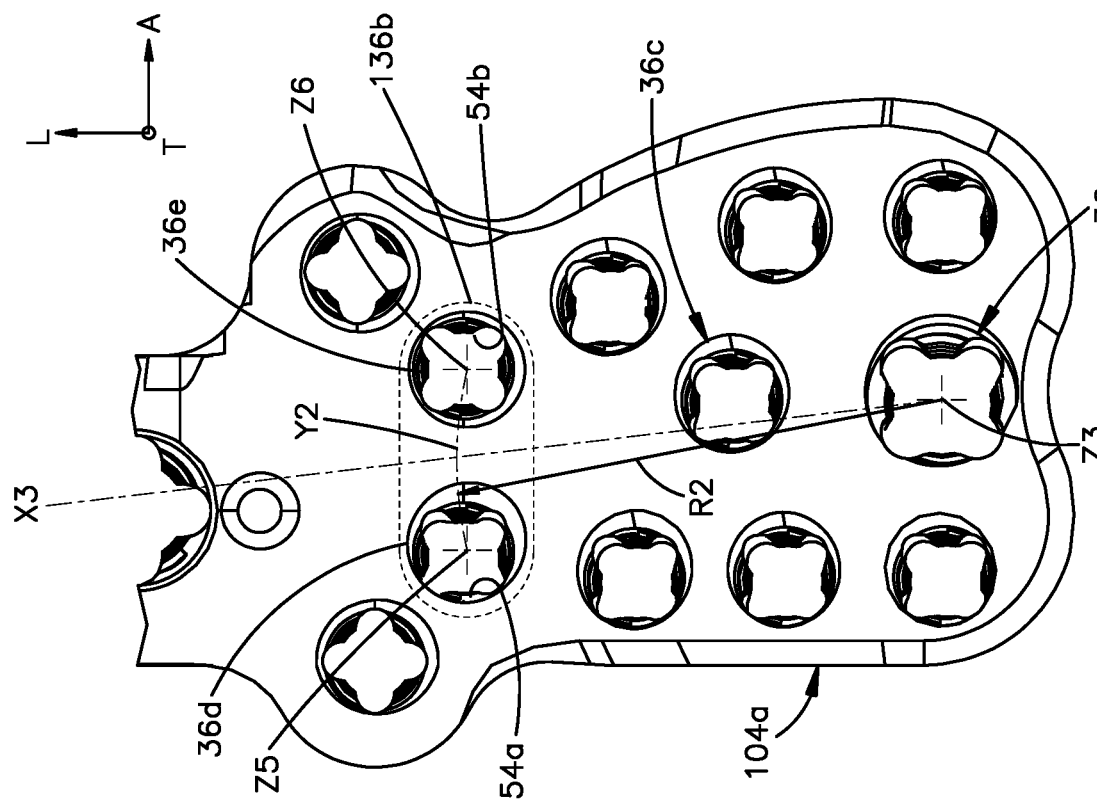

BONE PLATES, AND RELATED SYSTEMS AND METHODS

TECHNICAL FIELD

The present invention relates to bone plates, and more particularly to bone plates having angular adjustability relative to underlying anatomy.

BACKGROUND

Long-bone fractures, such as femoral and humeral fractures, are often treated with screws or other fixation devices inserted into or through a bone to stabilize fractured portions thereof once they have been brought into corrective alignment. Femoral bone fixation treatments can involve the insertion of an intramedullary (IM) nail into the medullary cavity of the femur and a subsequent insertion of bone fixation screw(s) into a condylar or trochanteric portion of the femur, depending upon whether the IM nail is inserted into the medullary canal at an antegrade or retrograde insertion trajectory. Antegrade insertion trajectories extend from the anatomical proximal end of the femur (i.e., at the hip joint), such as from the tip or slightly lateral to the tip of the greater trochanter, and into the medullary canal toward the anatomical distal end of the femur along the anatomical axis of the femur. Retrograde insertion trajectories extend from the anatomical distal end of the femur (i.e., at the knee joint) toward the anatomical proximal end of the femur and are effectively the opposite of antegrade insertion trajectories.

As used herein, the term "retrograde intramedullary nail" refers to an IM nail designed for retrograde insertion into the medullary canal. Retrograde IM nails are known to provide advantageous fixation to the distal portions of the femur (e.g., the distal condylar and intercondylar regions), such as for treating distal femur fractures. For example, retrograde IM nails allow for easier targeting and insertion of locking screws within locking holes at the trailing end of the nail, which resides within the distal femur. When treating distal femur fractures, retrograde femoral nailing can require additional bone fixation, particularly when the femur exhibits poor bone quality and/or in periprosthetic settings. In such instances, a supplemental locking attachment washer (LAW) or plate can be coupled to the trailing end of the nail via a plurality of bone screws. For simplicity and brevity, the locking attachment washers described below can each be referred to as a "plate." The plate defines one or more holes for bone screws that interconnect with the IM nail. Additionally, the plate can define one or more additional holes for additional bone screws that affix within portions of the femur adjacent the trailing end of the IM nail for supplemental bone fixation.

IM nails and associated plates can be provided at various sizes, geometries, and lengths to facilitate treatments of various types and indications of bone fractures. Additionally, physicians can select various IM nail and plate combinations based upon the treatment needs of the patient. For example, IM nails can be paired with plates having an increased length, such that the plate can extend from an end region of the bone (e.g., the condylar or trochanteric portion of the femur) to and alongside the shaft region of the bone. For such plates having increased length, the distal end of the plate should be fixed to the bone in alignment with the associated lengthwise portion of the IM nail.

The targeting and insertion of locking screws at the trailing end of the IM nail, and at the associated plate, is generally simplified by the fact that the nail trailing end and/or the associated plate can be directly engaged with instrumentation, such as an insertion handle and/or an aiming arm having aiming elements for targeting the locking holes near the trailing end of the IM nail. However, targeting locking holes at the leading end of an IM nail, however, is more challenging due to factors such as nail deflection and deformation that can result from stress and strain, particularly as the length of the nail increases. Furthermore, as the length of the plate increases, so to increases the challenges relating to aligning the distal end of the plate with the associated portion of the IM nail.

SUMMARY

According to an embodiment of the present disclosure, a bone fixation system includes an intramedullary nail and a bone plate. The intramedullary nail has a nail body elongate along a longitudinal direction. The nail body has a nail head and a distal locking portion spaced from the nail head in a distal direction along the longitudinal direction. The nail head defines a nail hole extending through the nail body along a transverse direction offset from the longitudinal direction. The bone plate has a plate body extending along a longitudinal plate axis and having first and second sides opposite each other along a lateral direction perpendicular to the longitudinal plate axis. The plate body has an outer surface and a bone-facing surface opposite each other. The plate body is alignable with the nail body such that: the longitudinal plate axis is oriented substantially along the longitudinal direction, the outer surface and bone-facing surface are spaced from each other along the transverse direction, and the lateral direction is offset from the longitudinal and transverse directions. The plate body defines a first plate hole and a second plate hole arrangement distally spaced from the first plate hole. The first plate hole and the second plate hole arrangement each extend from the outer surface to the bone-facing surface. The first plate hole is configured to receive a first locking member for insertion through the first plate hole and the nail hole for interconnecting the bone plate to the intramedullary nail. The second plate hole arrangement is configured to receive at least one second locking member. The plate body is configured to pivot along an angulation range about a central hole axis of the first plate hole when the first locking member extends through the first plate hole and further into the nail hole. The angulation range is configured for aligning the plate body with a distal portion of the nail body along the transverse direction. The angulation range is defined between laterally opposed ends of the second plate hole arrangement. The second hole arrangement is configured such that the at least one second locking member is configured to substantially secure the bone plate to the underlying bone at any selected angulation within the angulation range.

According to another embodiment of the present disclosure, a bone plate includes a plate body having a first end and a second end opposite each other along a longitudinal axis oriented along a longitudinal direction. The plate body has a first side and a second side opposite each other along a lateral direction offset from the longitudinal direction. The plate body has a bone-facing surface and an outer surface opposite each other along a transverse direction offset from the longitudinal and lateral directions. The plate body defines a first hole and a second hole arrangement each extending from the outer surface to the bone-facing surface. The second hole arrangement is spaced distally from the first hole along the longitudinal direction. The first hole is configured to receive a first fixation member for affixing with underlying bone. The second hole arrangement is configured to receive at least one second fixation member for affixing with underlying bone. The plate body is configured to pivot along an angulation range about the first fixation member extending through the first hole and into underlying bone. The second hole arrangement extends laterally across the longitudinal axis, defines the angulation range, and is configured such that the at least one second fixation member is configured to substantially secure the bone plate to the underlying bone at any selected angulation within the angulation range.

According to an additional embodiment of the present disclosure, a method for treating a bone includes inserting an intramedullary nail into a medullary canal of the bone and placing a bone plate alongside the bone. The bone plate has proximal and distal ends opposite each other along a longitudinal direction. The method includes inserting a first locking member through a first plate hole defined in a proximal portion of the bone plate, into underlying bone, and at least into a nail hole defined in the intramedullary nail, pivoting the bone plate about the first locking member until a portion of the bone plate distal of the proximal portion is aligned with a distal portion of the intramedullary nail, and inserting at least one fixation member through at least one fixation hole defined in the portion of the bone plate distal of the proximal portion and into underlying bone. The method includes inserting at least one second locking member through at least one second plate hole defined in the bone plate and into underlying bone adjacent the intramedullary nail and advancing the at least one second locking member through the at least one second plate hole such that a head of the at least one second locking member becomes fully seated in the at least one second locking hole. The at least one second plate hole is distally spaced from the first plate hole along the longitudinal direction. After the pivoting and aligning steps, the method includes further advancing the first locking member until a head thereof is fully seated in the first plate hole.

BRIEF DESCRIPTION OF THE DRAWINGS

The foregoing summary, as well as the following detailed description of illustrative embodiments of the present application, will be better understood when read in conjunction with the appended drawings. For the purposes of illustrating the features of the present application, there is shown in the drawings illustrative embodiments. It should be understood, however, that the application is not limited to the precise arrangements and instrumentalities shown. In the drawings:

FIG. 8 is an enlarged view of a locking hole of the plate head illustrated in FIG. 7;

FIG. 9 is a sectional end view of a portion of the plate head taken along section line IX-IX of FIG. 7, which section line intersects the locking hole illustrated in FIG. 8;

FIGS. 10 and 11 are top views of the plate head of FIG. 7 at a first angulated position (FIG. 10) and a second angulated position (FIG. 11) relative to underlying anatomy;

FIGS. 12 and 13 are sectional end views of the plate head, taken along section line IX-IX of FIG. 7, at the first angulated position (FIG. 12) and the second angulated position (FIG. 13) relative to the underlying anatomy;

FIG. 14 is a top plan view showing the bone plate angulated at the first and second angulated positions relative to underlying anatomy;

FIG. 16 is a top plan view of a plate head portion of the bone plate illustrated in FIG. 15;

FIG. 17 is a bottom plan view of a proximal (structurally proximal but anatomically distal) portion of the nail-plate construct illustrated in FIG. 15;

DETAILED DESCRIPTION OF ILLUSTRATIVE EMBODIMENTS

Figure 1:
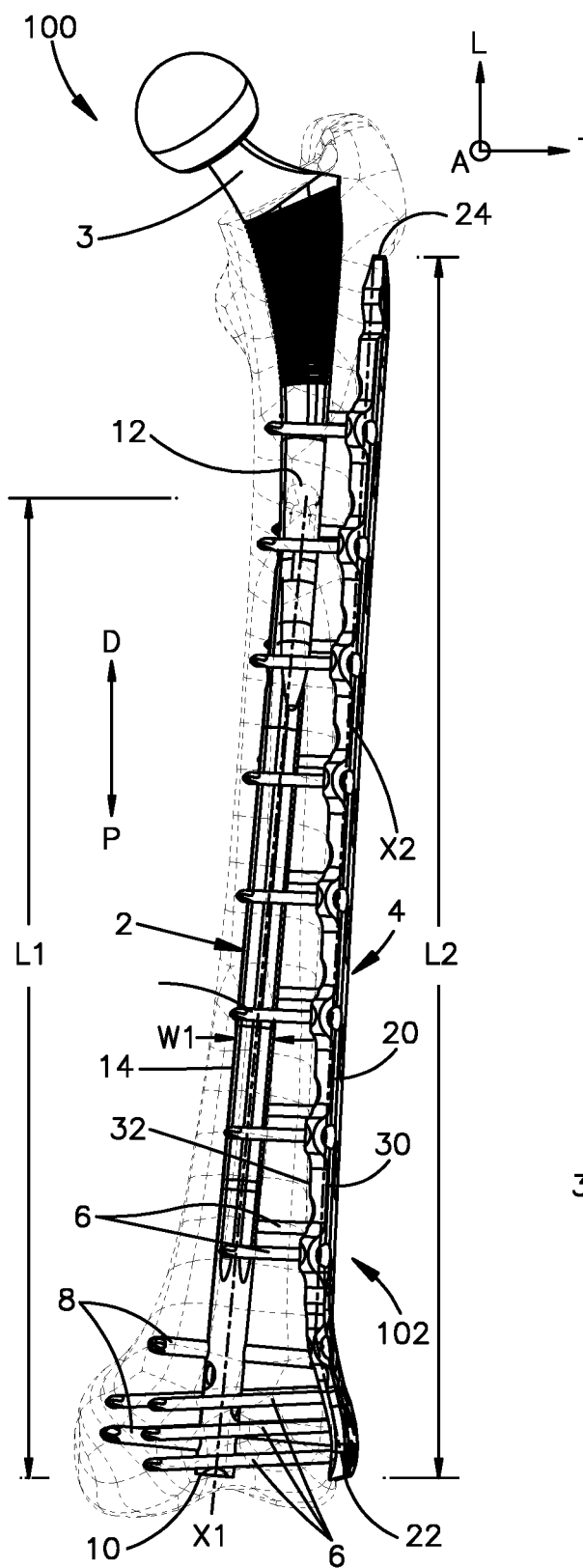
FIG. 1 is a side view of a bone fixation system including a nail-plate construct that includes an IM nail interconnected with a bone plate, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately", "about", and "substantially", as used herein with respect to dimensions, angles, ratios, and other geometries, takes into account manufacturing tolerances. Further, the terms "approximately", "about", and "substantially" can include 10% greater than or less than the stated dimension, ratio, or angle. Further, the terms "approximately", "about", and "substantially" can equally apply to the specific value stated.

It should be understood that, although the terms first, second, etc. may be used herein with reference to various features, these features should not be limited by these terms other than to distinguish one feature from another. For example, a first feature could be termed a second feature in another context, and, similarly, a second feature could be termed a first feature in another context, without departing from the scope of the embodiments disclosed herein.

The embodiments disclosed herein pertain to bone plates that are adapted to facilitate plate angulation with underlying anatomy and/or underlying implant hardware for enhancing bone fixation. For example, the bone plates described herein have a hole structure that facilitates plate angulation about a pivot axis and also facilitates plate fixation at the desired angular orientation relative to the underlying anatomy and/or implant hardware. The example embodiments described below include bone fixation systems that include an intramedullary (IM) nail and a bone plate having a hole structure that allows the bone plate to interconnect with the IM nail, angulate relative to the IM nail to align the bone plate with the IM nail along their lengths, and then affix the bone plate with the underlying bone and the IM nail at the desired plate angulation. Bone plates having such angular adjustability are particularly advantageous because it can allow a single bone plate to be used with different IM nails of varying sizes and bend angles, which can greatly simplify the plate selection process and the overall surgical procedure. Additionally, the bone plates described herein can also be used without an associated IM nail and still provide the angular adjustability with underlying Referring now to FIGS. 1-3, an exemplary embodiment of a bone fixation system 100 includes an intramedullary (IM) nail 2 insertable within the medullary canal of a long bone 1, a bone plate 4 affixable to an outer surface of the bone 1 and connectable to the IM nail 2, and a plurality of fixation members 6, 8 for coupling the bone plate 4 to the IM nail 2, thereby forming an interconnected nail-plate construct (NPC) 102, and for affixing the nail-plate construct 102 to the bone 1. The nail-plate construct 102 can also be configured to treat periprosthetic conditions, including for affixing with an existing implant or prosthesis 3. For example, the nail-plate construct 102 is shown in a periprosthetic environment providing inter-prosthetic affixation with a femoral stem 3 from a previous osteotomy. It should be appreciated that the foregoing represents one non-limiting example of a particular treatment that the plate-nail construct 102 can provide. Additionally, although the long bone 1 discussed with reference to the illustrated embodiments is a femur, it should be appreciated that the bone fixation system 100 can be adapted for use with other long bones, such as a tibia, fibula, humerus, radius, and ulna, by way of non-limiting examples. Additionally, although the IM nail 2 shown in the illustrated embodiments is configured for retrograde femoral insertion, the bone fixation system 100 can be adapted for use with antegrade insertion trajectories.

The IM nail 2 has a first end 10 and a second end 12 spaced from each other along a longitudinal direction L. In the illustrated embodiment, which shows a retrograde femoral IM nail, the longitudinal direction L generally extends along the cranial-caudal direction of patient anatomy. In such embodiments, the first end 10 is the proximal end of the nail 2 and is configured to temporarily couple with insertion instrumentation, such as an insertion arm. The second end 12 is the distal end of the nail 2 and is the leading or forward end of the nail 2 during insertion within the medullary canal. The second end 12 is spaced from the first end 10 in a distal direction D, while the first end 10 is spaced from the second end 12 in a proximal direction P that is opposite the distal direction D. It should be appreciated that the distal and proximal directions P, D are each mono-directional components of the longitudinal direction L, which is bi-directional.

The IM nail 2 defines a nail length L1 measured between the first and second ends 10, 12 along the longitudinal direction L. The IM nail 2 also defines a nail width W1 measured along a direction perpendicular to the longitudinal direction. The bone fixation system 100 can include IM nails 2 of various lengths L1 widths W1 for selective use for various types of bone fractures, as described below.

It should also be appreciated that, as used herein: the terms "longitudinal", "longitudinally", and derivatives thereof refer to the longitudinal direction L; the terms "distal", "distally", and derivatives thereof refer to the distal direction D; and the terms "proximal", "proximally", and derivatives thereof refer to the proximal direction P. Furthermore, because retrograde insertion trajectories essentially place the structural (implant) uses of the directional terms "proximal" and "distal" into opposition with these terms' anatomical usage (e.g., the "proximal" end of the IM nail 2 resides in the "distal" femur, while the "distal" end of the nail is spaced toward the "proximal" femur) directions, for purposes of clarity, the terms "proximal" and "distal" and their derivatives are used herein to refer to directional aspects of the synthetic structural components of the bone fixation system 100, unless, however, these terms are used with specific reference to anatomy (e.g., the "proximal femur, "distal femur", "distal anatomical direction"), in which latter case the terms refer to the anatomical directions.

The IM nail 2 has a nail body 14 that extends along a central nail axis X1 that is generally oriented along the longitudinal direction L. The central nail axis X1 need not be linear; preferably, the central nail axis X1 follows a path that is substantially coextensive with the anatomical axis of the bone 1. Thus, the central nail axis X1 can have one or more straight portions and one or more curved portions. The nail body 14 includes a proximal locking portion 2a (also referred to herein as the "nail head" 2a) that extends distally from the first end 10, an intermediate portion 2b (also referred to herein as the "main shaft portion" 2b) that extends distally from the nail head 2a, and a distal locking portion 2c that extends from the main shaft portion 2b to the second end 12 of the nail 2. The nail head 2a is configured to attach to instrumentation, such as an insertion handle, for inserting the nail 2 into the medullary canal.

Figure 3:
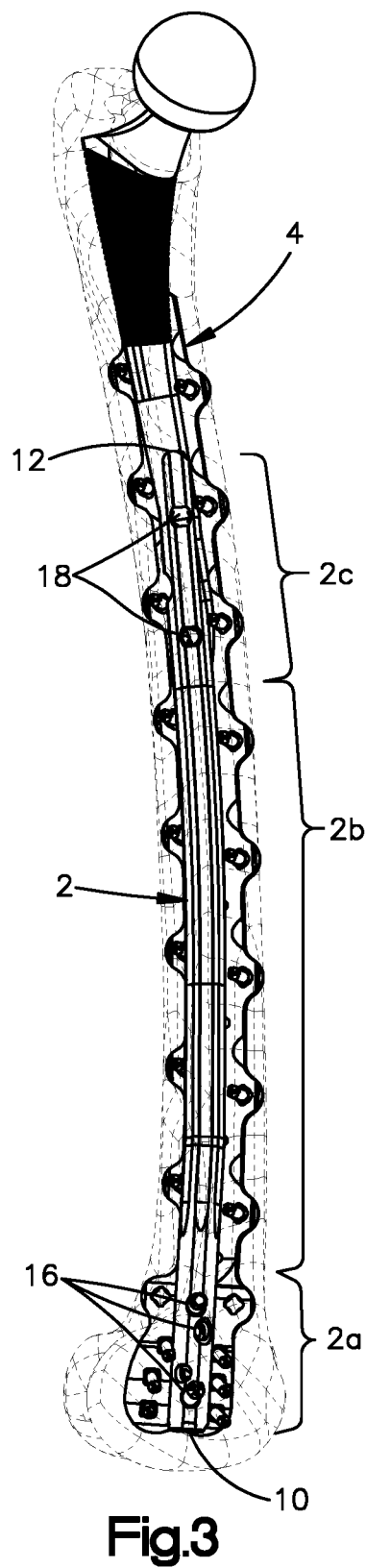
FIG. 3 is a bottom view of the bone fixation system illustrated in FIG. 1.

The nail head 2a also defines one or more proximal locking holes 16 extending through the nail body 14 along one or more respective central hole axes oriented along one or more various directions that are offset from the longitudinal direction L. These directions can be perpendicular or oblique to the longitudinal direction L. Each proximal locking hole 16 is preferably configured to receive a fixation member, particularly a locking member 8, such as a bone screw or a spiral blade, that extends through the respective hole 16 and affixes the nail head 2a to adjacent portions of the bone 1, such as the distal femur in the illustrated embodiment. The proximal locking hole(s) 16 and associated bone fixation members can also be employed for affixing one or more fractured portions of the adjacent bone to one another. The proximal locking holes 16 of the IM nail are described in more detail below. As shown in FIG. 3, the distal locking portion 2c of the IM nail 2 also defines one or more distal locking holes 18 that extend through the nail body 14 along one or more various directions that are offset from the longitudinal direction L (which directions can be perpendicular or oblique to the longitudinal direction L. Each distal locking hole 18 is configured to receive a corresponding fixation member 8, such as a bone screw or a spiral blade, for affixing the distal locking portion 2c of the IM nail 2 to adjacent portions of the bone 1.

Figure 2:
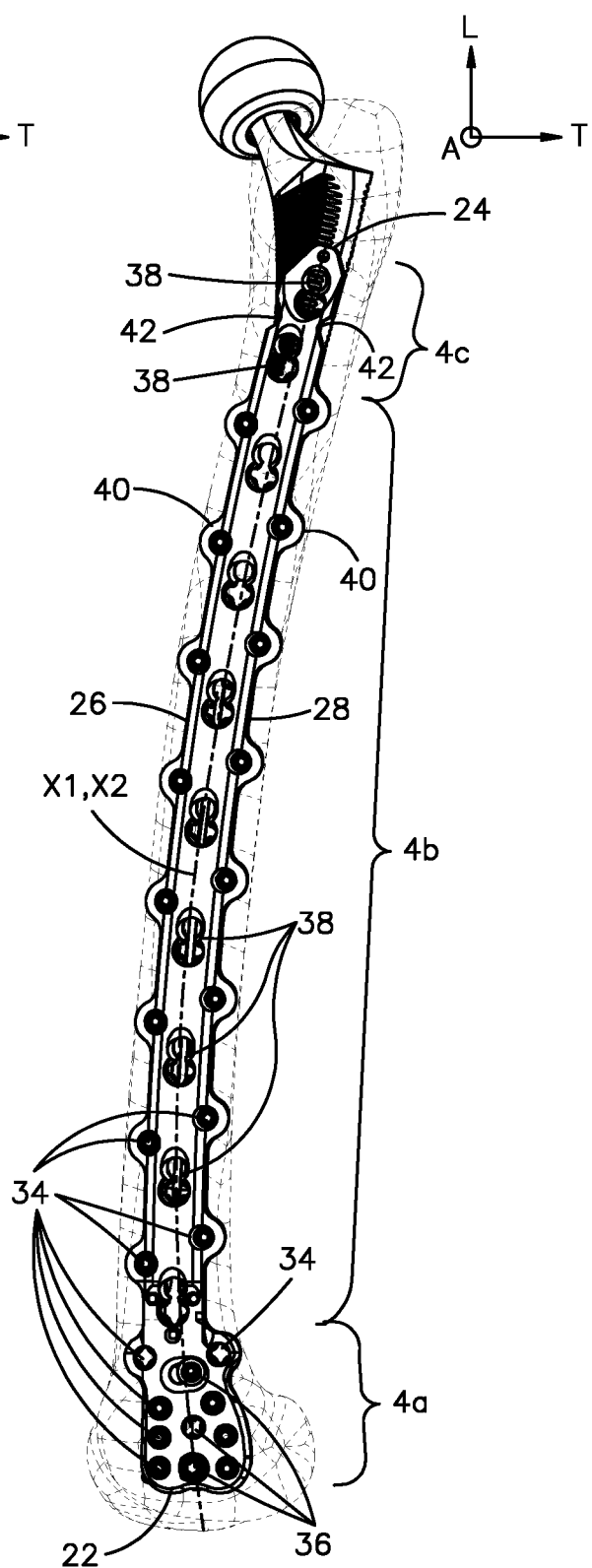
FIG. 2 is a top view of the bone fixation system illustrated in FIG. 1.

With continued reference to FIGS. 1-3, the bone plate 4 has a plate body 20 that extends from a first end 22 to a second end 24 spaced from the first end 22 along the longitudinal direction L. The bone plate 4 defines a plate length L2 measured between the first and second ends 22, 24 along the longitudinal direction L. The IM nail 2 and the bone plate 4 can be provided at various configurations and sizes (e.g., nail length L1, nail width W1, plate length L2) adapted for treating various conditions. For example, the IM nail 2 and bone plate 4 can be tailored as needed to form various nail-plate constructs 102 adapted for treating supracondylar fractures (including those with intra-articular extension), combinations of ipsilateral condylar and diaphyseal fractures, ipsilateral femoral/tibial fractures, femoral fractures in multiple-trauma patients, periprosthetic fractures (including Type B1 and Type C according to the Vancouver classification system, and also including interprosthetic fractures), fractures in morbidly obese patients, fractures in osteoporotic and osteopenic bone, impending pathological fractures, malunions, and non-unions, by way of non-limiting examples. It should be appreciated that the nail-plate construct 102 can be adapted as needed to treat various other conditions. The nail length L1 can be in a range of about 120 mm to about 500 mm. The nail width W1 can be in a range of about 8 mm to about 16 mm. The plate length L2 can be in a range of about 120 mm to about 550 mm.

The plate body 20 also has a first side 26 and a second side 28 opposite each other along a lateral direction A that is offset from the longitudinal direction L. In the illustrated embodiment, the lateral direction A of the bone plate 4 generally extends along the anterior-posterior direction of patient anatomy. The plate body 20 includes an outer surface 30 and a bone-facing surface 32 opposite each other along a transverse direction T that is offset from the longitudinal and lateral directions L, A. In the illustrated embodiment, the transverse direction T of the bone plate 4 generally extends along the medial-lateral direction of patient anatomy. Although the illustrated embodiment shows the longitudinal, lateral, and transverse directions L, A, T being substantially perpendicular to each other, in other embodiments the longitudinal, lateral, and transverse directions L, A, T need not be perpendicular to each other. For example, in such other embodiments, one or more of the longitudinal, lateral, and transverse directions L, A, T can be oblique to one or both of the other directions L, A, T. The bone facing surface 32 of the plate body 20 preferably has a contoured geometry that corresponds to the outer surface of the bone 1. The plate body 20 defines a plurality of plate fixation holes 34, 36, 38 that extend from the outer surface 30 to the bone facing surface 32. The plate fixation holes 34, 36, 38 are configured to receive various fixation members 6, 8 for affixing the bone plate 4 to the IM nail 2 and/or to the bone 1, as described in more detail below.

The bone plate 4 defines a longitudinal plate axis X2 that extends generally along the longitudinal direction L. As shown, the longitudinal plate axis X2 need not be linear. Preferably, the longitudinal plate axis X2 extends along a path that follows the contours of the outer surface of the bone 1, as shown in FIGS. 1-2. Additionally, the longitudinal plate axis X2 also preferably tracks the underlying central nail axis X1 when the bone plate 4 is properly coupled to the nail 2, as described in more detail below. Thus, when viewed along the transverse direction T at proper plate-to-nail coupling, the longitudinal plate axis X2 substantially superimposes upon the central nail axis X1, as shown in FIG. 2.

The plate body 20 includes a proximal plate portion 4a (also referred to herein as the "plate head" 4a) that extends distally from the first end 22, an intermediate plate portion 4b (also referred to herein as the "plate shaft" 4b) that extends distally from the plate head 4a, and a distal plate portion 4c that extends distally from the plate shaft 4b to the second end 24 of the bone plate 4. The plate head 4a, plate shaft 4b, and distal plate portions 4c have respective geometries that correspond to the associated bone anatomy. In the illustrated example for fixation to the distal femur, the plate head 4a geometry corresponds to the lateral condyle and epicondyle of the distal femur, the plate shaft 4b geometry corresponds to the femoral shaft, and the distal plate portion 4c geometry corresponds to the lateral portions of the sub trochanteric, trans trochanteric, and trochanteric regions of the proximal femur. In other embodiments, and depending on the plate length L2, the plate shaft 4b and distal plate portion 4c can be adapted to correspond to different anatomical regions of the bone.

The plate fixation holes 34, 36, 38 include bone fixation holes 34, proximal locking holes 36, and additional holes 38, which have various purposes and are configured to receive various types of fixation members 6, 8, as will now be described.

Figure 4:
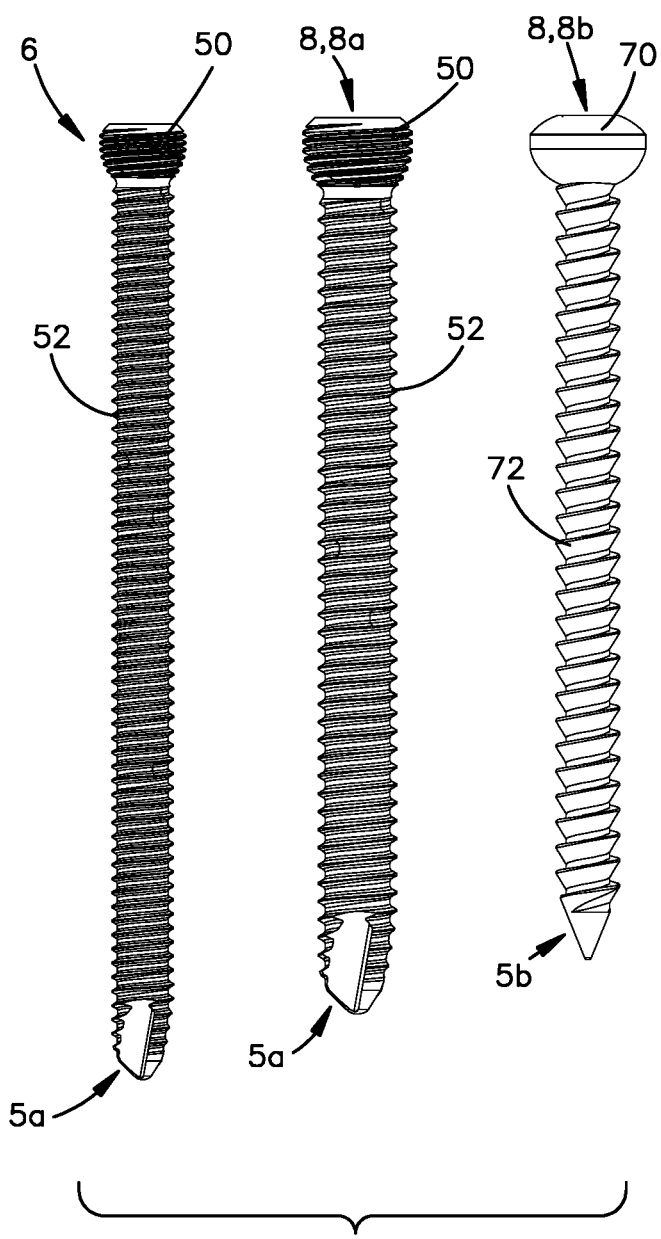
FIG. 4 is a side view of fixation members employable in the bone fixation system illustrated in FIGS. 1-3.
Figure 6:
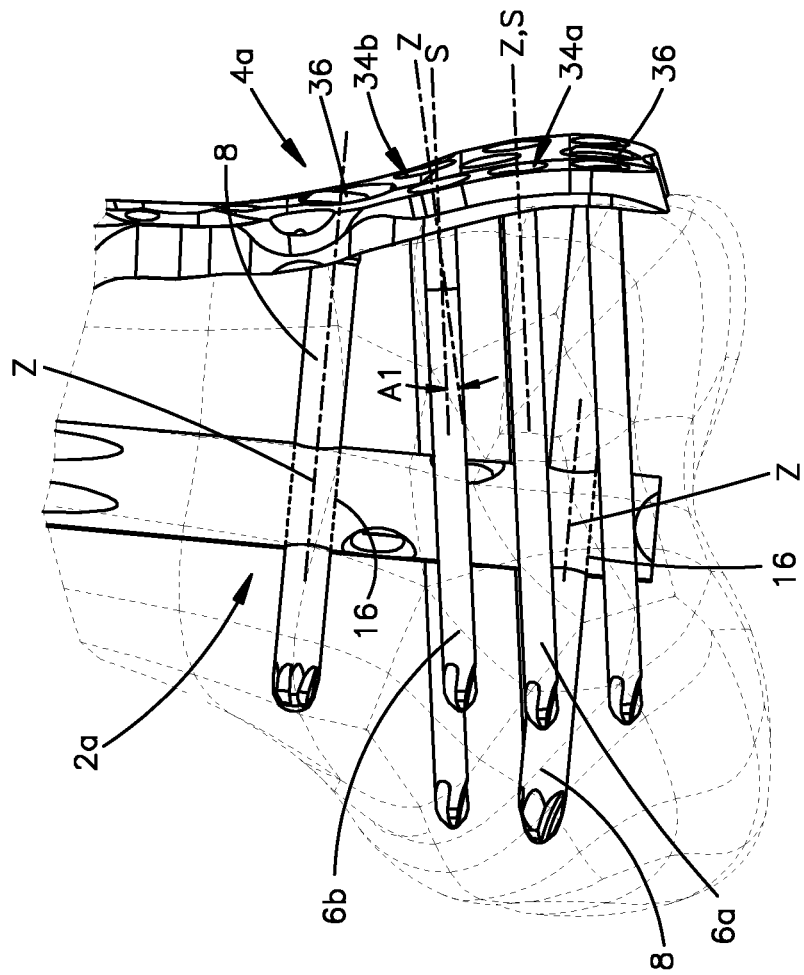
FIGS. 5 and 6 are an enlarged top view (FIG. 5) and side view (FIG. 6) of a proximal (structurally proximal but anatomically distal) portion of the bone fixation system illustrated in FIGS. 1 and 2.
Figure 5:
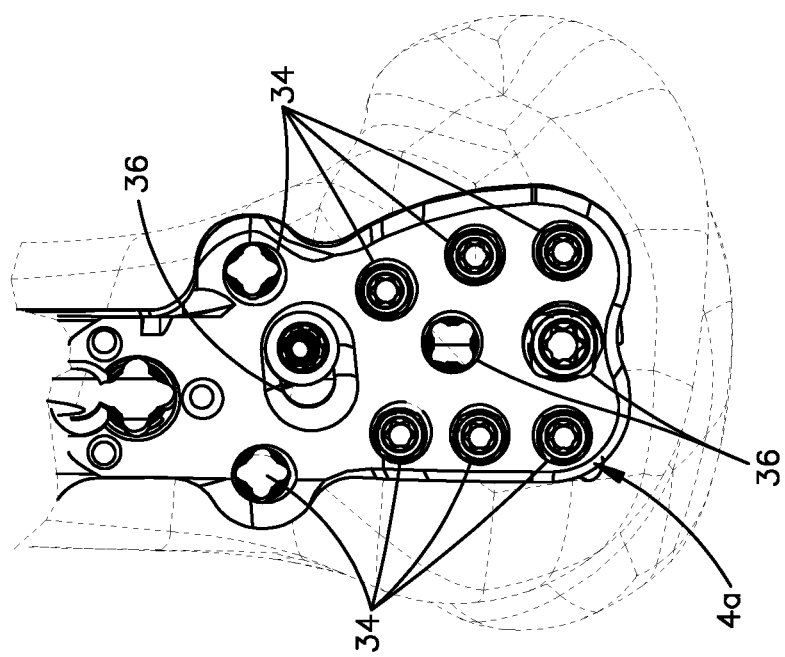

Referring now to FIGS. 4-6, the fixation members include locking members 8, which are configured to extend through aligned locking holes 36, 16 of the bone plate 4 and IM nail 2, respectively, thereby forming the interconnected nail-plate construct 102. The fixation members also include bone fixation members 6 that are configured to extend through a bone fixation hole 34 and into underlying portions of bone without extending through the IM nail 2. It should be appreciated that locking members 8 and the bone fixation members 6 both facilitate fixation with the bone adjacent the IM nail 2 and the bone plate 4. The locking members 8 and bone fixation members 6 can include bone screws, such as locking head bone screws 5a having a head 50 that includes external threading configured to lock with interior locking features of a fixation hole when the head 50 is fully seated in the hole. The locking head bone screws 5a include a threaded shaft 52 that extends from the head 50 along a screw axis S and is configured to advance through and affix with bone. The locking head bone screws 5a shown in FIG. 4 are variable angle locking (VAL) bone screws, which are configured to lock within a fixation hole at either a nominal orientation, whereby the screw axis S is substantially colinear with the central hole axis Z (see bone fixation member 6a and hole 34a in FIG. 6), or an "angulated" orientation, whereby the screw axis S is oriented at an acute angle A1 (also referred to herein as the "angulation" A1) with respect to the central hole axis Z (see bone fixation member 6b and hole 34b in FIG. 6). It should be appreciated, however, that one or more of the bone fixation members 6 and/or locking members 8 can employ standard-type locking screws 5a that are configured to lock within a fixation hole substantially only at a nominal orientation. Additionally, as shown, one or more of the locking members 8 and/or bone fixation members 6 can be a compression bone screw 5b having a head 70 with a smooth outer surface and a threaded shaft 72 extending from the head 70 along a screw axis S. Additionally or alternatively, one or more of the locking members 8 can be a spiral blade, locking bolt, or another type of locking member for interlocking with a locking hole 16, 18 of the IM nail 2.

Referring now to FIGS. 1-3 and 5-6, the bone fixation holes 34 are configured to receive bone fixation members 6 that extend from the bone fixation holes 34 and into underlying portions of bone that are spaced laterally from the IM nail 2 so as not to mechanically interfere with the IM nail 2. To avoid such mechanical interference, the bone fixation holes 34 are preferably laterally offset from the longitudinal plate axis X2 such that the bone fixation members 6 can be inserted therethrough along opposite sides of the IM nail 2 (see FIGS. 1, 3, and 5). Accordingly, the bone fixation holes are also referred to herein as "offset holes" 34. As shown, some of the offset holes 34 can be defined along the plate head 4a for affixing within the condylar and intercondylar regions of the distal femur. Additional ones of the offset holes 34 can be defined along the plate shaft 4b for affixing within the femoral shaft. In additional embodiments, one or more additional offset holes 34 can be defined within the distal plate portion 4c, such as for affixing within upper portions of the femoral shaft and/or the proximal femur, depending upon the plate length L2. The plate body 20 can include lateral protrusions or tabs 40 extending outwardly from the first and second sides 26, 28 along the plate head 4a and the plate shaft 4b. The lateral tabs 40 can define portions of the offset holes 34. In this manner, the lateral tabs 40 can increase the lateral spacing of the offset holes 34 and thus also of the bone fixation members 6. The bone fixation holes 34 are preferably variable angle locking (VAL) holes 34 and the bone fixation members 6 are preferably VAL bone screws, although one or more of the bone fixation holes 34 can be a standard-type locking hole or a compression hole.

As shown in FIG. 2, the additional fixation holes 38 can include combi-holes, such as those that combine variable angle (VA) holes and locking compression plate (LCP) holes, which combi-holes can be referred to as "VA LCP" combi-holes 38. In this manner, each additional fixation hole 38 can be employed selectively with a VAL bone screw, a compression bone screw, and/or a locking member (such as for locking with a distal locking hole 18 of the IM nail 2), as needed. The additional fixation holes 38 of the plate shaft 4b are preferably centrally aligned along the longitudinal plate axis X2, although in other embodiments one or more of the additional fixation holes 38 of the plate shaft 4b can be eccentrically positioned with respect to the longitudinal plate axis X2. As shown, the distal plate portion 4c can include one or more additional fixation holes 38, which are preferably eccentrically positioned with respect to the longitudinal plate axis X2. The distal plate portion 4c can also include additional features, such as for aiding with reconstruction of associated portions of the bone. In the illustrated example, the distal plate portion 4c includes a pair of recesses or notches 42 extending laterally inward from the first and second sides 26, 28 of the plate body 20. The notches 42 are configured to increase the ability of the distal plate portion 4c to be manipulated for bending and contouring to the associated bone anatomy, such as for matching the contours of the greater trochanter in the illustrated example.

As shown in FIGS. 5-6, the proximal locking holes 36 are preferably defined in the plate head 4a and are configured to receive locking members 8 (e.g., locking screws, spiral blades, locking bolts, and the like) that extend through the proximal locking holes 36 of the bone plate 4 and interconnect with the nail head 2a. As shown, the locking members 8 can extend from the proximal locking holes 36 of the bone plate 4 and further through the proximal locking holes 16 of the IM nail 2. In this manner, the locking members 8 directly interconnect the plate head 4a to the nail head 2a (thus also interconnecting the bone plate 4 to the IM nail 2). In other embodiments (described below with reference to FIGS. 15-17), one or more of the locking members 8 can extend through one or more respective proximal locking holes 36 of the bone plate 4 and from there they can extend alongside one or more respective portions of the nail head 2a in bracketing fashion, which can provide another mode of direct interconnection between the plate head 4a and nail head 2a.

The IM nail 2 and bone plate 4 can employ various hole sizes for use with bone fixation members 6 and locking members 8 of various sizes and configurations. For example, the bone fixation members 6 can be locking head bone screws 6 (preferably VAL screws 6) having major shaft diameters in a range of about 2.5 mm to about 6.0 mm, and preferably in a range from about 3.0 mm to about 4.0 mm. The locking members 8 can include VAL screws and one or more compression screws having major shaft diameters in a range of about 3.8 mm to about 8.0 mm, and preferably in a range from about 4.0 mm to about 5.5 mm. The bone fixation members 6 and locking members 8 can have lengths in a range of about 35 mm to about 125 mm, which lengths can be selected based upon various factors, including the underlying region of the bone and the intended screw angulation. For example, longer lengths can be selected for bone fixation members 6 and locking members 8 for insertion through holes 34, 36 of the plate head 4a (and into the underlying condylar or intercondylar regions) and shorter lengths can be selected for bone fixation members 6 to be inserted into bone fixation holes 34 of the plate shaft 4b (and into the underlying the bone shaft). It should be appreciated that the foregoing dimensions can also be scaled upward or downward in size based upon different treatment needs.

Figure 7:
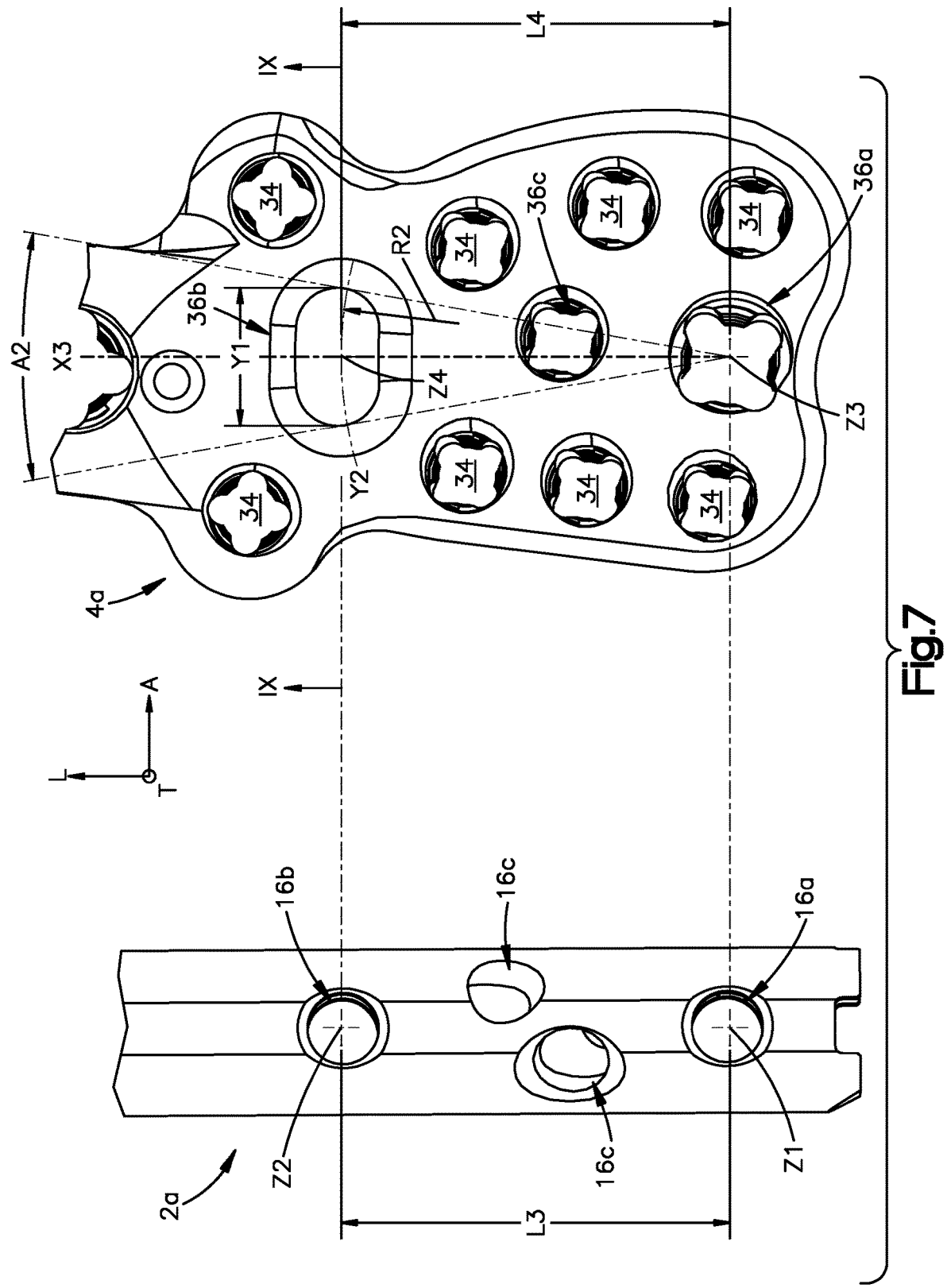
FIG. 7 is a plan, partially exploded view of associated proximal portions of the IM nail and bone plate shown in FIG. 1, which portions are referred to herein as the "nail head" and "plate head," respectively, according to an embodiment of the present disclosure.

Referring now to FIG. 7, the proximal locking holes 16 of the nail head 2 include first and second proximal locking holes 16a,b that are configured to facilitate coupling with associated proximal locking holes of the bone plate 4. The first and second proximal locking holes 16a,b of the nail head 2a extend through the nail head 2a along respective central hole axes Z1, Z2, which are preferably parallel but can alternatively be non-parallel. The first and second proximal locking holes 16a,b are spaced from each other at a nail hole spacing distance L3, as measured between their respective central hole axes Z1, Z2 along the longitudinal direction L. The proximal locking holes 36 of the plate head 4a include a first hole 36a adjacent the first end 22 and a second hole arrangement 36b spaced from the first hole 36a in the distal direction D. The first hole 36a and the second hole arrangement 36b are configured to facilitate coupling with the IM nail 2. The first hole 36a extends through the plate head 4a along a central hole axis Z3. For illustrative purposes, a plate head reference axis X3 is shown that intersects the central hole axes Z3, Z4 of the first hole 36 and second hole arrangement 36b. The second hole arrangement 36b defines a lateral dimension Y1 measured along an arrangement axis Y2 that extends generally along the lateral direction A. The second hole arrangement 36b also defines a central transverse axis Z4 that extends through the bone plate 4 substantially along the transverse direction T and is located at a lateral midpoint of the lateral dimension Y1. In the illustrated embodiment, the plate head reference axis X3 intersects the arrangement axis intersects Y2 substantially at a midpoint thereof. The first hole 36a and the second hole arrangement 36b are spaced from each other at a plate hole spacing distance L4, as measured longitudinally between the central hole axis Z3 of the first hole 36a and the central transverse axis Z4 of the second hole arrangement 36b. It should be appreciated that the plate head 4a can include one or more additional proximal locking holes 36 for aligning with one or more additional proximal locking holes 16 of the IM nail 2. For example, the plate head 4a can include a third locking hole 36c, which can be configured to receive a locking member 8 insertable therethrough and further through a third proximal locking hole 16c in the nail head 2a for increasing the locking fixation between the plate head 4a and nail head 2a.

The nail and plate hole spacing distances L3, L4 can be in a range of about 15 mm to about 40 mm, and more particularly in a range of about 20 mm to about 35 mm, and more particularly in a range of about 25 mm to about 30 mm. In one non-limiting example embodiment, the nail and plate hole spacing distances L3, L4 are each about 27.5 mm. The nail and plate hole spacing distances L3, L4 are preferably substantially equidistant, which provides significant benefits for interlocking fixation between the plate head 4a and the nail head 2a. For example, in the presently illustrated embodiment, such equidistant spacing allows the first holes 36a, 16a of the plate head 4a and nail head 2a to be aligned with each other while the second hole arrangement 36b of the plate head 4a is aligned with the second hole 16b of the nail head 2a. In this manner, a first locking member 8a can be inserted through the first locking holes 36a, 16a of the plate head 4a and nail head 2a and a second locking member 8b can be inserted through the second locking arrangement 36b and further through the second hole 16b of the plate head 4a and nail head 2a, respectively.

Referring now to FIGS. 7-14, the proximal locking holes 36 of the bone plate 4 are also configured to provide the bone plate 4 with angular adjustability for angular alignment with the IM nail 2. In state of the art IM nail-to-plate fixation procedures, as the nail length and bend angle increases, so does the difficulty with aligning the plate shaft (particularly the distal portion thereof) with the distal portion of the IM nail. The proximal locking holes 36 described herein provide a solution to this technical challenge by providing the second hole arrangement 36b that allows a surgeon to pivot the bone plate 4 side-to-side about a pivot axis substantially along the transverse direction T to a desired angular orientation that matches the position of the IM nail 2, and then to employ the second hole arrangement 36b to affix the plate head 4a to the nail head 2a at the desired orientation. In the present embodiment, the bone plate 4 is pivotable side-to-side in guided fashion along an angulation range A2 substantially along the lateral direction A, which generally corresponds to the anterior-posterior anatomical direction. After the bone plate 4 is angularly oriented to match the position of the IM nail 2, the second hole arrangement 36b further facilitates locking the bone plate 4 to the IM nail 2 at the desired plate orientation. Such plate angular adjustability is particularly advantageous because it can allow a single bone plate 4 to be used with various IM nails 2 of different sizes and bend angles, which can greatly simplify the associated surgical procedures.

In the present embodiment, the central hole axis Z3 of the first hole 36a substantially defines the pivot axis for the plate angulation and, as described in more detail below, the second hole arrangement 36b guides and controls the pivot angulation. The first hole 36a is preferably a VAL hole and the first locking member 8a is preferably a VAL screw, the shaft 52 of which is configured to advance along screw axis S1 through the first hole 36a, through underlying bone, and into the first proximal hole 16a of the IM nail 2. The shaft 52 preferably has a length sufficient to extend into cortical bone on the far side of the IM nail 2 when the head 50 is fully seated in the first hole 36a, thereby enhancing fixation of the interconnected nail-plate construct with the bone. The use of a VAL locking hole a VAL bone screw for the first hole 36a and the first locking member 8a is particularly advantageous because it allows a measure of tolerance for locking the first locking member 8a through the first hole 36a of the bone plate 4 and the first proximal locking hole 16a of the IM nail 2 even if the holes 36a, 16a are not precisely aligned.

The second hole arrangement 36b extends along the lateral direction A and provides a first lateral bound 54a and a second lateral bound 54b that are laterally spaced from each other. In the present embodiment, the second hole arrangement 36b is a guide slot 36b that extends along a slot path along the arrangement axis Y2 between the first and second lateral bounds 54a,b, which define the lateral ends the guide slot 36b. In such embodiments, the central transverse axis Z4 represents the central hole axis Z4 of the guide slot 36b. The guide slot 36b is configured to receive a shaft 72 of the second locking member 8b inserted substantially transversely through the guide slot 36b and into underlying bone. As shown in FIGS. 10-14, when the first locking member 8a extends through the first holes 36a, 16a of the plate and nail heads 4a, 2a and the second locking member 8b extends through the guide slot 36b and the second locking hole 16b of the plate and nail heads 4a, 2a, the guide slot 36b allows the bone plate 20 to toggle back and forth along the angulation range A2 between first and second angular positions M1, M2, at which positions M1, M2 the first and second lateral bounds 54a,b abut against opposite sides of the screw shaft 72 of the second locking member 8b. Accordingly, the first and second lateral bounds 54a,b can be referred to as the "toggle ends" 54a,b of the guide slot 36b. For illustrative purposes, FIGS. 10-11 show relative positions between the plate head reference axis X3 and an anatomical reference axis X0 at the first and second angular positions M1, M2. The angulation range A2 provided by the first hole 36a and the guide slot 36b can be from about 0 degrees to about 20 degrees, and more particularly from about 2 degrees to about 15 degrees, and more particularly from about 6 degrees to about 10 degrees. In one non-limiting example embodiment, the angulation range is from about 7 degrees to about 9 degrees. After the bone plate 4 is angulated to the desired orientation, the first and second locking members 8a,b can be further advanced into the bone until their heads 50, 70 are fully seated in the first hole 36a and guide slot 36b, respectively, thereby rigidly affixing the bone plate 4 to the underlying bone and to the IM nail 2 at the desired orientation. Thus, the guide slot 36b is configured so that the second locking member 8b can substantially secure the bone plate 4 to the underlying bone at any selected angulation within the angulation range A2.

As shown in FIGS. 7-8, the guide slot 36b can be a curved guide slot 36b extending along a curved guide path (i.e., along a curved arrangement axis Y2) that defines an arc length C1, as measured along the arrangement axis Y2 between the first and second toggle ends 54a,b (see FIG. 8). The curved arrangement axis Y2 preferably has a constant radius R2, as measured from the central hole axis Z3 of the first hole 36a. The radius R2 of the arrangement axis Y2 is preferably substantially equivalent to hole spacing distances L3, L4, which facilitates accurate guided angulation of the bone plate 4 relative to the IM nail 2. Thus, a ratio of the radius R2 of the arrangement axis Y2 to the nail and plate hole spacing distances L3, L4 can be about 1:1. The arc length C1 can be in a range have a minimum value substantially equivalent to the major shaft diameter of the second locking member 8b and a maximum value of about 20.0 mm, and more particularly in a range of about 5.5 mm to about 10.0, and more particularly in a range of about 6.5 mm to about 8.0 mm. Additionally, the guide slot 36b defines a slot width W2, as measured between opposed slot side walls 56a,b along a direction that is perpendicular to the arrangement axis Y2 in a plane substantially orthogonal to the central hole axis Z4. The slot width W2 can be substantially equivalent but slightly greater than the major diameter of the screw shaft 72, such that the guide slot 36b facilitates guided plate angulation about the pivot axis Z3.

As shown in FIGS. 8-9, the guide slot 36b extends transversely through the plate head 4a from an upper hole perimeter 58 at a boundary with the outer surface 30 of the plate body 20 to a lower hole perimeter 60 at a boundary with the bone-facing surface 32 of the plate body 20. The guide slot 36b can have a hole geometry similar to that of a compression slot. In such embodiments, the plate body 20 defines a countersink surface 62 (also referred to herein as a "countersink" 62) within the guide slot 36b, which countersink 62 extends transversely from the upper hole perimeter 60 to a slot wall surface 64 which, in turn, extends transversely from the countersink 62 toward the lower hole perimeter 60. The guide slot 36b can also include one or more relief or undercut surfaces 66 extending transversely from the slot wall surface 64 to the lower hole perimeter 60. Preferably, the countersink 62 is smooth and unthreaded and the second locking member 8b is preferably a compression screw having a smooth head 70 that defines a head profile that is complimentary with the countersink profile. The shaft 72 of the second locking member 8b extends along a screw axis S2 and is configured to advance through the guide slot 62b, through underlying bone, and into the second proximal hole 16b of the nail head 2a until the screw head 70 is fully seated within the guide slot 36b. Similar to the first locking member 8a, the shaft 72 of the second locking member 8b preferably has a length sufficient to extend into cortical bone on the far side of the IM nail 2, thereby enhancing fixation of the interconnected nail-plate construct with the bone. Also similar to the first locking member 8a, the second locking member 8b is preferably capable of insertion within the guide slot 36b at an angulated insertion trajectory (i.e., relative to central hole axis Z4), which facilities extending through both of the guide slot 36b and the second proximal locking hole 16b of the IM nail, even if the holes 36b, 16b are not precisely aligned.

It should be appreciated that although the guide slot 36b of the present embodiment has a countersink 62 and is configured to receive a compression screw 8b, the guide slot 36b preferably is not configured to facilitate dynamic compression (i.e., longitudinal and/or lateral plate translation relative to the compression screw 8b and underling bone). Instead, the compression screw 8b and the guide slot 36b of the present embodiment are configured to facilitate the plate angulation and subsequently affix the plate 4 at the desired orientation within the angulation range A2. It should also be appreciated that, in embodiments in which the guide slot 36b includes a countersink 62, the plate angulation range A2 can alternatively be bounded by contact between the ends of the countersink 62 and the head 70 of the second locking member 8b. It should also be appreciated that in other embodiments the guide slot 36b need not have a countersink 62 similar to that of a compression slot, but can have other slot designs.

In one non-limiting example embodiment of the nail-plate construct 102, the plate hole spacing distance L4 and the arrangement axis radius R2 are each about 27.5 mm, the offset holes 34 are each VAL holes, the bone fixation members 6 are each VAL bone screws having a major shaft diameter of about 3.5 mm, the first locking member 8a is a VAL bone screw having a major shaft diameter of about 5.0 mm, the second locking member 8b is a compression screw having a major shaft diameter of about 4.5 mm, the third proximal locking hole 36c is a VAL hole, and the third locking member 8c is a VAL bone screw having a major shaft diameter of about 3.5 mm. It should be appreciated that various other hole and fixation member 6, 8 configurations are within the scope of the present embodiments. It should be appreciated that these parameters, and those described elsewhere in this disclosure, can be adapted as needed.

Figure 15:
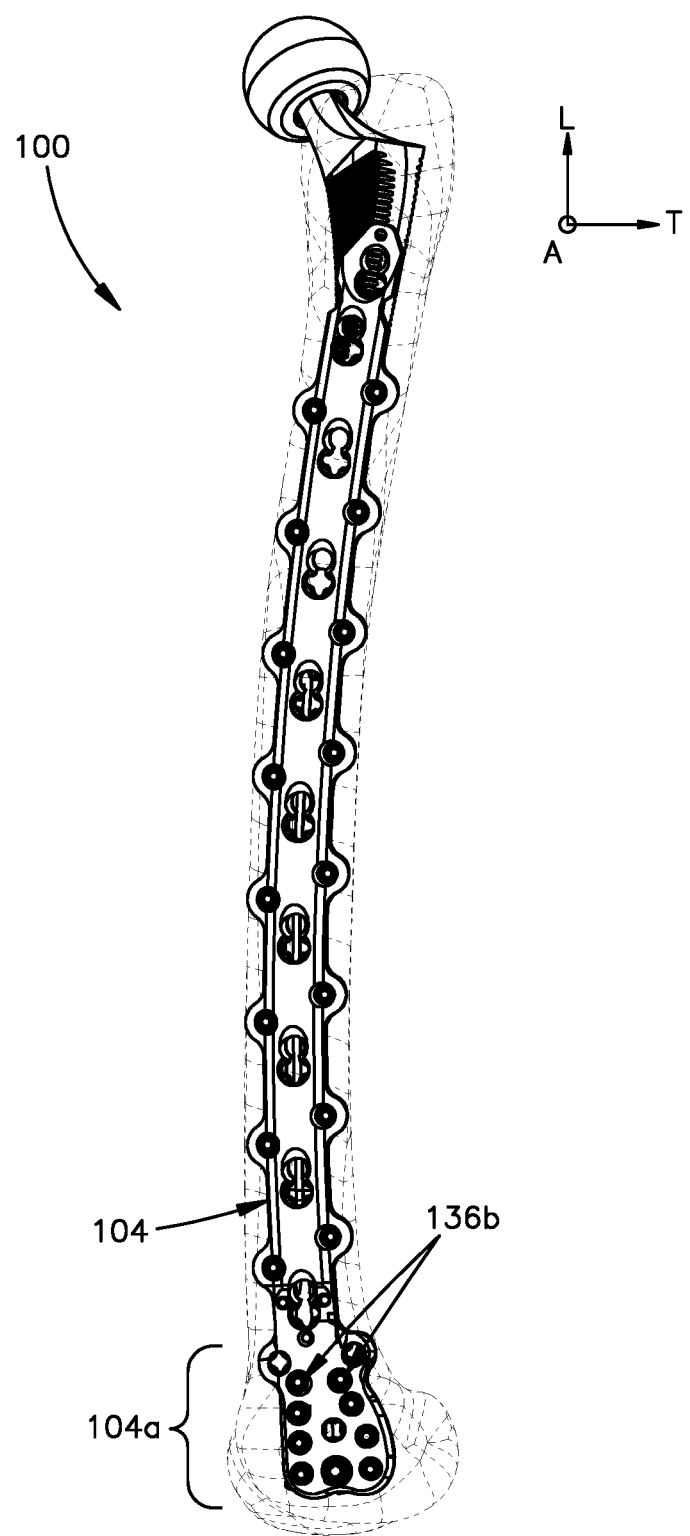
FIG. 15 is a top view of a bone fixation system including a nail-plate construct that includes a bone plate having a variant design, according to another embodiment of the present disclosure.

Referring now to FIGS. 15-17, another embodiment of the bone fixation system 100 will now be described in which a bone plate 104 has a plate head 104a having a modified second hole arrangement 136b. The bone plate 104 of this additional embodiment is otherwise similar to the bone plate 4 described above. Moreover, in this additional embodiment, other features of the bone fixation system 100 are otherwise similar to the manner in which they are described above with reference to the embodiment shown in FIGS. 1-14. Thus, for such similar features, the same reference numbers will be used in FIGS. 15-17. In the present embodiment, the second hole arrangement 136b includes a pair of second locking holes 36d,e that are laterally spaced from each other along the arrangement axis Y2, which, as above, extends generally along the lateral direction A. In this additional embodiment, the first and second lateral bounds 54a,b of the second hole arrangement 136b are defined by the furthest opposed sides of the second locking holes 36d,e along the arrangement axis Y2. The pair of second locking holes 36d, e are configured to receive respective second locking members 8d,e that extend therethrough and further alongside opposite sides of the nail head 2a in a manner bracketing or blocking the opposite sides of the nail head 2a. In this manner, the second locking members 8d, e can be placed in contact with, or close proximity to, the opposite sides of the nail head 2a (see FIG. 17), while the first locking member 8a extends from the first hole 36a of the plate head 104 and interlocks with the first proximal locking hole 16a of the nail head 2a, as described above. Thus, in the present embodiment, the first locking member 8a and the pair of second locking members 8e,d interconnect the plate head 4a with the nail head 2a (and thus interconnect the bone plate 104 with the IM nail 2).

The pair of second locking holes 36d, e are preferably VAL holes and the pair of second locking members 8e, d are preferably VAL bone screws. The second locking holes 36e,d are located such that their respective central holes axes Z5, Z6 intersect the arrangement axis Y2. Similar to the embodiment described above, the arrangement axis Y2 preferably extends along a curved path having a radius R2 that is substantially constant and substantially equivalent to the nail hole spacing distance L3. The arrangement axis Y2 can be configured as described above with reference to FIG. 7. The bone plate 104 of the present embodiment is configured to allow angulation relative to the underlying bone and the IM nail 2. In this embodiment, the first locking member 8a is inserted through the first hole 36a of the plate head 4a and into the first proximal locking hole 16a of the nail head 2a, but with the screw head 50 not fully seated in the first hole 36a, similar to the manner described above. With the first locking member 8a partially inserted in this manner, the bone plate 104 can be pivoted about the shaft 50 of the first locking member 8a as needed until the plate shaft 4b is aligned with the nail main shaft 2b and distal locking portion 2c, optionally with the assistance of fluoroscopy. After the bone plate 104 is angulated into proper alignment with the IM nail 2, the pair of second locking members 8d, e can be inserted through the pair or second locking holes 8d,e at respective screw angulations A1 that bring their respective screw shafts 50 alongside opposite sides of the nail head 2a. In this manner, the pair of second locking members 8d,e, once fully inserted, can effectively block the IM nail 2 from toggling along the lateral direction (and thus substantially along the anterior-posterior direction) after fixation.

The VAL configuration of the second locking holes 36d, e and the second locking members 8d,e allows the second locking members 8d,e to be inserted at screw angulations that facilitate the blocking configuration with the nail head 2a, even at various plate angulations within the plate angulation range A2. It should be appreciated that the plate angulation range A2 of the present embodiment can be substantially equivalent to the embodiment described above. In the present embodiment, the second locking members 8d,e can each be a VAL bone screw having a major diameter of about 3.5 mm or about 5.0 mm, although the second locking members 8d,e can be sized according to the other screw sizes described above.

It should also be appreciated that in additional embodiments, the bone fixation systems 100 described above can be provided in a kit that includes a plurality of interchangeable IM nails 2, bone plates 4, 104, and fixation members 6, 8 having different sizes and configurations, thereby allowing surgeons to select the particular combinations of IM nail 2, bone plate 4, 104, and fixation members 6, 8 to treat a particular condition.

Example methods of using the bone fixation system 100 for surgical repair will now be described. Although these methods involve surgical repair of a using a retrograde femoral IM nail 2, the methods can be adapted for use with antegrade IM nails and/or other long bones, such as the tibia, fibula, humerus, radius, and ulna, by way of non-limiting examples. Example method 200 employs the bone plate 4 described above with reference to FIGS. 1-14; and example method 300 employs the bone plate 104 described above with reference to FIGS. 15-17.

Figure 18:
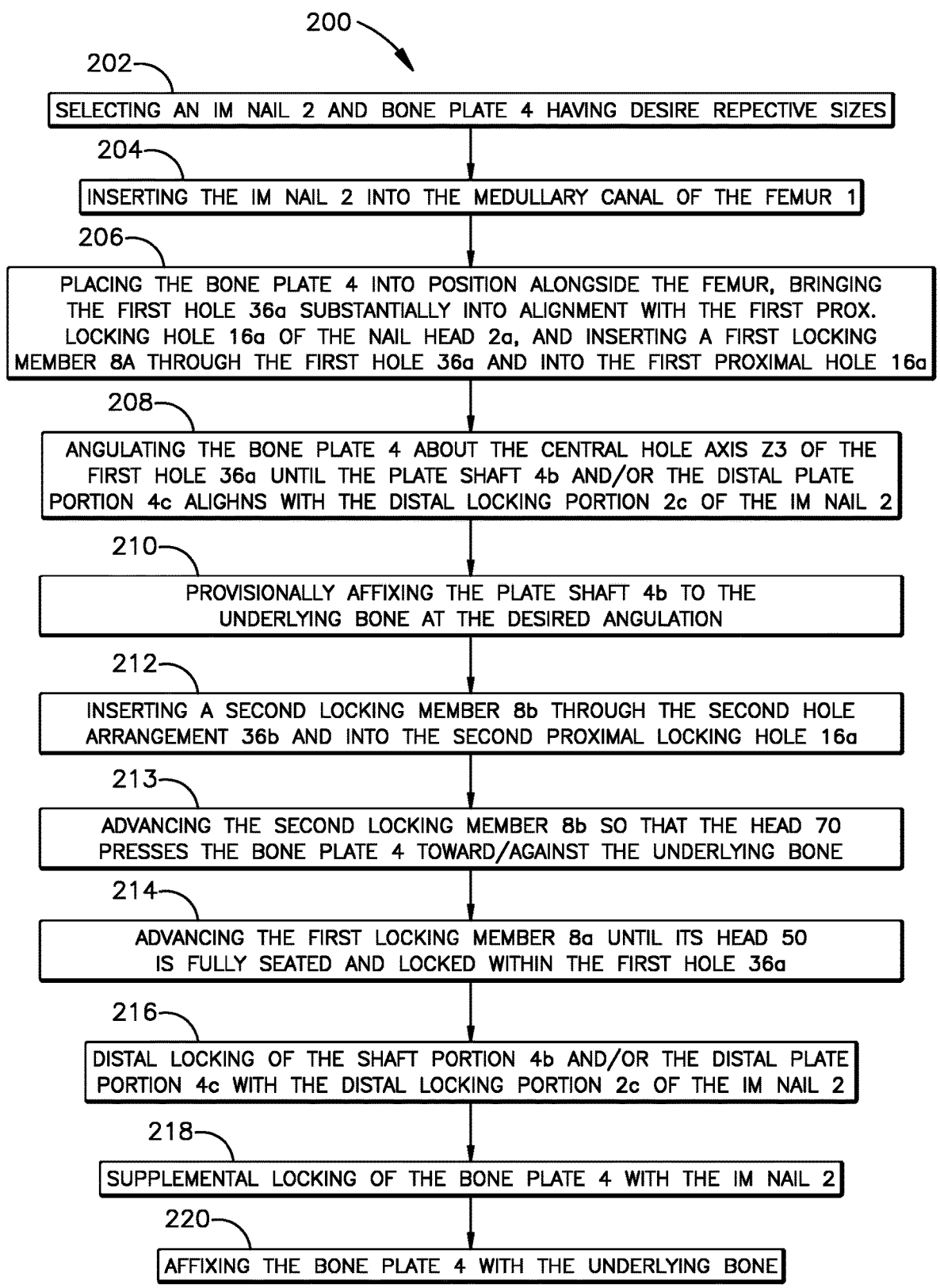
FIG. 18 is a process diagram showing method steps for using the bone fixation system illustrated in FIGS. 1-14.

Referring now to FIG. 18, method 200 includes step 202, during which the surgeon selects an IM nail 2 and bone plate 4 having respective sizes (e.g., nail length and width L1, W1 and plate length L2) and geometries suitable for the femoral repair. The surgeon can determine the appropriate nail length L1 and width W1 using techniques known in the art, such as by viewing radiopaque rulers, such as a length ruler and a diameter ruler, placed adjacent the femur 1 under fluoroscopy.

At step 204, the surgeon inserts the IM nail 2 into the medullary canal of the femur 1 from an entry point at the distal femur, such as at the top of the intercondylar notch. The surgeon can perform various preparatory steps before step 204, such as locating the entry point, inserting a guide member, such as a guide wire (e.g., k-wire), into the medullary canal through the entry point, opening the medullary canal by advancing a canal-opening device (e.g., a drill bit and/or awl), along the guide wire, optionally expanding or "reaming" the medullary canal in preparation for receiving the IM nail 2, loading the IM nail 2 onto an insertion instrument (e.g., insertion handle), and optionally loading the IM nail 2 into the guide member or optional reamer. If necessary, the surgeon can employ an impaction hammer for the insertion instrument to insert the IM nail 2 to the final desired longitudinal position within the medullary canal. During the insertion process, the surgeon can monitor the IM nail 2 position using fluoroscopy to ensure proper alignment and longitudinal positioning.

When the surgeon has determined that the IM nail 2 is inserted at the desired longitudinal position within the medullary canal, the surgeon can commence step 206, which includes initial locking, i.e., partially locking the plate head 4a to the nail head 2a at the distal femur. At step 206, the surgeon places the bone plate 4 into position alongside the femur and brings the first hole 36a of the plate head 4a substantially into alignment with the first proximal locking hole 16a of the nail head 2a. This step can be performed with the assistance of targeting instrumentation, such as fluoroscopy and/or guide members attachable to the insertion instrument. With the first hole 36a of the plate head 4a substantially aligned with the first proximal locking hole 16a of the nail head 2a, the surgeon inserts the first locking member 8a through the first hole 36a, into underlying bone, and into the first proximal locking hole 16a of the nail head 2a. In this example, the first locking member 8a is a VAL bone screw. During step 206, the surgeon preferably stops short of advancing the first locking member 8a to its fully seated position within the first holes 36a, thereby allowing the bone plate 4 to pivot about the partially inserted first locking member 8a during subsequent steps, as described below.

At step 208, the surgeon angulates the bone plate 4 about the pivot axis (which is the central hole axis Z3 of the first hole 36a, through which the shaft 52 of the partially inserted first locking member 8a extends) until bone plate 4 is at the desired angulation relative to the underlying bone and/or the underlying IM nail. For example, the desired angulation can be when the plate shaft 4b and/or the distal plate portion 4c aligns with the distal locking portion 2c of the IM nail 2 such that the offset holes 34 are laterally spaced from the IM nail 2. During step 208, the surgeon can confirm that when the bone plate 4 is at the desired angulation, the second hole arrangement 36b (which is the guide slot 36b in this example) is substantially aligned with the second proximal locking hole 16b of the nail head 2a. As with step 206, the surgeon can also perform step 208 with the assistance of targeting instrumentation.

At step 210, with the bone plate 4 at the desired angulation relative to the underlying anatomy, the surgeon can provisionally affix the plate shaft 4b to the underlying bone at the desired angulation. This can include affixing at least one bone fixation member 6 through at least one respective offset hole 34 in the plate shaft 4b and into underlying bone alongside the IM nail 2.

At step 212, with the bone plate 4 at the desired angulation and with the second hole arrangement 36b substantially aligned with the second proximal locking hole 16b of the nail head 2a, the surgeon inserts the second locking member 8b through the guide slot 36b, into underlying bone, and into the second proximal locking hole 16b of the nail head 2a. In this example, the second locking member 8b is compression bone screw. During step 212, the surgeon can advance the second locking member 8b through the guide slot 36b until the head 70 abuts the countersink 62. Additionally, at step 213, the surgeon can further advance the second locking member 8b so that the head 70 presses the bone plate 4 toward and/or against the underlying bone, thereby minimizing any gap between the bone plate 4 and the bone 1, which can reduce soft tissue irritation at the plate-bone interface.

If needed during steps 206 and 212, such as when precise alignment of holes 36a, 16a and/or of holes 36b, 16b is not feasible, the surgeon can insert the first and/or second locking member 8a,b at an angulated screw insertion trajectory through one or both of the respective holes of the plate head 4a and nail head 2a.

At step 214, the surgeon further advances the first locking member 8a until the head 50 thereof is fully seated and locked within the first hole 36a of the plate head 4a. In this example, step 214 includes locking the head 50 of the first locking member 8a with interior locking structures of the first hole 36a.

With the plate 4 properly aligned with the underlying IM nail 2 and the first and second locking members 8a,b interconnecting the plate head 4a with the nail head 2a, the surgeon can perform step 216, which includes distal locking, which can include inserting one or more distal locking members 8 through one or more aligned pairs of holes 38, 18 in the shaft portions 4b, 2b and/or distal portions 4c, 2c of the plate 4 and IM nail 2. Additionally or alternatively, the distal locking step 216 can include affixing a pair of bone fixation members 6 through a respective pair of offset holes 34 in the plate shaft 4b and into underlying bone alongside the IM nail 2, thereby blocking the associated portion of the IM nail 2 from lateral movement.

At step 218, the surgeon can perform supplemental locking, which can include supplemental locking of the plate head 4a with the nail head 2a. During this step, the surgeon can optionally insert a third locking member 8c through a third hole 36c in the plate head 4a and a third proximal locking hole 16c in the nail head 2a. Additionally or alternatively, step 216 can include distal locking of the plate shaft 4b and/or distal plate portion 4c with the distal locking portion 2c of the IM nail 2.

At step 220, the surgeon can perform fixation of the bone plate 4 with the underlying bone, which can occur at the plate head 4a, the plate shaft 4b, and or the distal plate portion 4c. This step can include inserting one or more bone fixation members 6 through one or more of the respective offset holes 34 in the bone plate 4 and into underlying bone alongside the IM nail 2.

Figure 19:
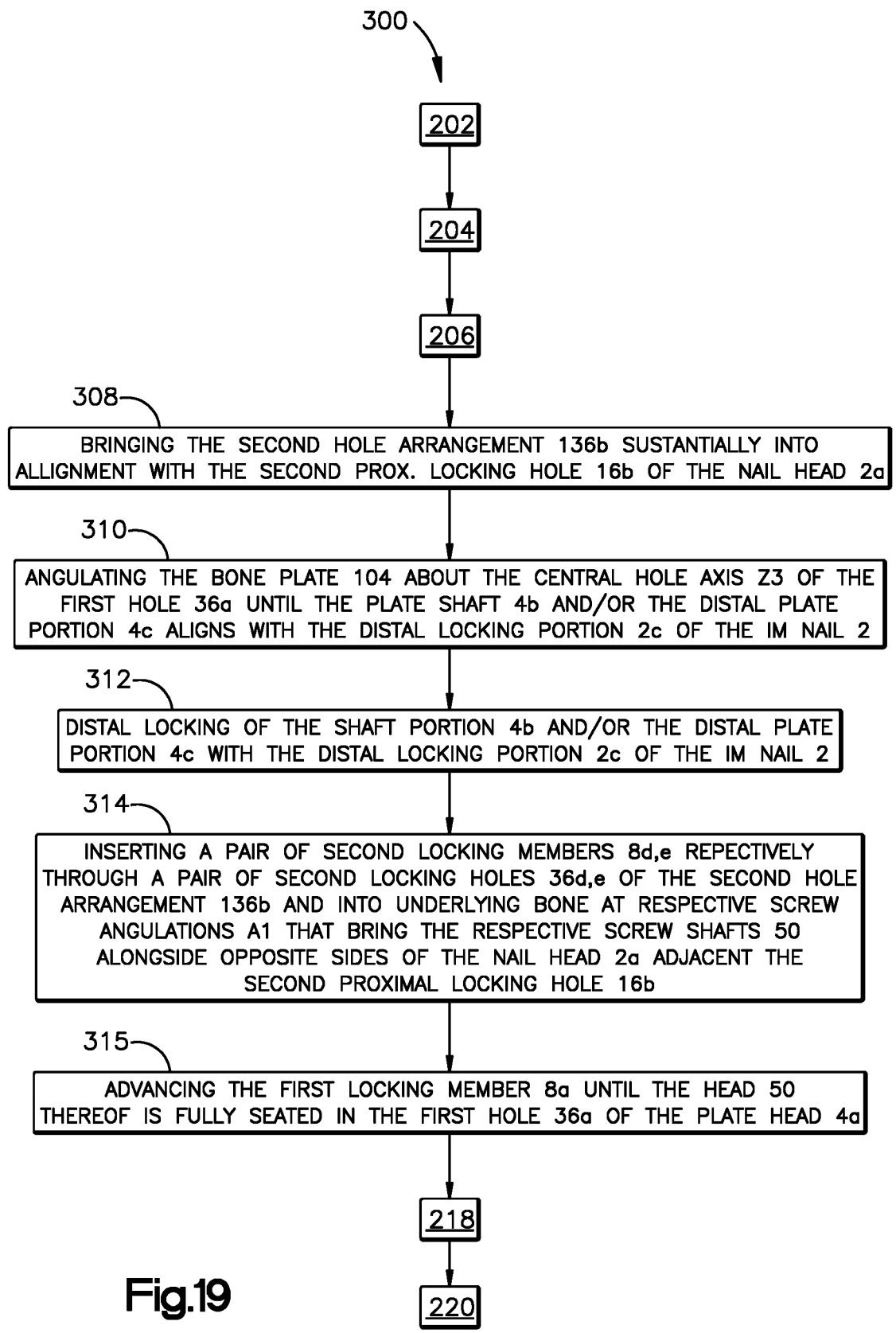
FIG. 19 is a process diagram showing method steps for using the bone fixation system illustrated in FIGS. 15-17.

Referring now to FIG. 19, a method 300 of using the bone fixation system 100 shown in FIGS. 15-17 will now be described. For the sake of brevity, the following description of method 300 will focus on steps that are different than those of method 200. Method 300 includes step 202, 204, and 206 described above.

At step 308, after the first locking member 8a has been inserted through the first hole 36a of the plate head 104a, into underlying bone, and into the first proximal locking hole 16a of the nail head 2a, the surgeon brings the second hole arrangement 136b (which in this example is the pair of second locking holes 8d, e) substantially into alignment with the second proximal locking hole 16b of the nail head 2a. Bringing the second hole arrangement 136b substantially into alignment with the second proximal locking hole 16b can include bringing the arrangement axis Y2 between first and second lateral bounds 54a,b substantially into alignment with the second proximal locking hole 16b. As with step 206, the surgeon can also perform step 308 with the assistance of targeting instrumentation.

At step 310, the surgeon angulates the bone plate 104 about the pivot axis (which is the central hole axis Z3 of the first hole 36a, through which the shaft 52 of the partially inserted first locking member 8a extends) until the plate shaft 4b and/or the distal plate portion 4c aligns with the distal locking portion 2c of the IM nail 2.

After such alignment is attained during step 310, the surgeon performs step 312, which includes distal locking, which can include inserting one or more distal locking members 8 through one or more aligned pairs of holes 38, 18 in the shaft portions 4b, 2b and/or distal portions 4c, 2c of the plate 4 and IM nail 2. Additionally or alternatively, the distal locking step 312 can include affixing a pair of bone fixation members 6 through a respective pair of offset holes 34 in the plate shaft 4b and into underlying bone alongside the IM nail 2, thereby blocking the associated portion of the IM nail 2 from lateral movement.

Also after step 310, the surgeon performs step 314, which includes locking the second hole arrangement 136b to the nail head 2a. At step 314, the surgeon inserts the pair of second locking members 8d,e through the pair of second locking holes 36d,e, respectively, and into underlying bone at respective screw angulations A1 that bring the respective screw shafts 50 alongside opposite sides of the nail head 2a adjacent the second proximal locking hole 16b. In this manner, the pair of second locking members 8d,e, once fully seated in the second locking holes 36d,e, can effectively block the nail head 2a from toggling along the lateral direction (and thus substantially along the anterior-posterior direction) after fixation. In this example, the pair of second locking members 8d,e are each VAL bone screws.

At step 315, the surgeon further advances the first locking members 8a until the head 50 thereof is fully seated in the first hole 36a of the plate head 4a. In this example, step 316 includes locking the head 50 of the first locking member 8a with interior locking structures of the first hole 36a.

During method 300, preferably after steps 312 and 314, and 315, the surgeon can perform steps 216 and 218, which are described above.

It should be also appreciated that the foregoing methods are provided as examples, and that the surgeon can elect to adjust the sequence of various steps, omit one or more of the steps, and/or perform one or more additional steps, as needed.

It should further be appreciated that the bone plates 4, 104 described above can be employed to treat a bone without the use of an accompanying IM nail. In such embodiments, the second hole arrangement 36b, 136b can be employed to facilitate plate angulation A2 (pivoting about a first locking member 8a partially inserted through the first hole 36a and into underlying bone) for proper plate alignment with underlying bone, in similar fashion as described above. In yet further embodiments, the bone plates 4, 104 described above can be employed with other types of implants, such as a second bone plate on an opposite side of a bone, for facilitating angulation A2 of the bone plate 4, 104 about a first locking member 8a partially inserted through the first hole 36a and into a hole or other structure of the second bone plate.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. In particular, one or more of the features from the foregoing embodiments can be employed in other embodiments herein. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone fixation system, comprising:
an intramedullary nail having a nail body elongate along a longitudinal direction, the nail body having a nail head and a distal locking portion spaced from the nail head in a distal direction along the longitudinal direction, the nail head defining a nail hole extending through the nail body along a transverse direction offset from the longitudinal direction; and a bone plate having a plate body extending along a longitudinal plate axis and having first and second sides opposite each other along a lateral direction perpendicular to the longitudinal plate axis, the plate body having an outer surface and a bone-facing surface opposite each other, wherein the plate body is alignable with the nail body such that (1) the longitudinal plate axis is oriented substantially along the longitudinal direction, (2) the outer surface and bone-facing surface are spaced from each other along the transverse direction, and (3) the lateral direction is offset from the longitudinal and transverse directions;

the plate body defining a first plate hole and a second plate hole arrangement distally spaced from the first plate hole, the first plate hole and the second plate hole arrangement each extending from the outer surface to the bone-facing surface, wherein the first plate hole is configured to receive a first locking member for insertion through the first plate hole and the nail hole for interconnecting the bone plate to the intramedullary nail, and the second plate hole arrangement is configured to receive at least one second locking member, wherein the plate body is configured to pivot along an angulation range about a central hole axis of the first plate hole when the first locking member extends through the first plate hole and further into the nail hole, the angulation range configured for aligning the plate body with a distal portion of the nail body along the transverse direction, the angulation range defined between laterally opposed ends of the second plate hole arrangement, and wherein the second plate hole arrangement is configured such that the at least one second locking member is configured to substantially secure the bone plate to an underlying bone at any selected angulation within the angulation range.

2. The bone fixation system of claim 1, wherein the angulation range is from about 2 degrees to about 15 degrees.

3. The bone fixation system of claim 1, wherein the second plate hole arrangement of the plate body comprises a single, curved guide slot that extends between the laterally opposed ends along a curved slot axis having at least a directional component along the lateral direction, the at least one second locking member is a bone screw configured to extend through the curved guide slot and further into a second nail hole defined in the nail body, and the second nail hole is spaced from the nail hole in the distal direction.

4. The bone fixation system of claim 3, wherein a distance between the central hole axis of the first plate hole and the curved slot axis is substantially equivalent to a distance between central hole axes of the nail hole and the second nail hole.

5. The bone fixation system of claim 3, wherein the curved slot axis has a radius in a range from about 15 mm to about 40 mm, as measured from the central hole axis of the first plate hole, wherein the radius is substantially constant along the curved slot axis.

6. The bone fixation system of claim 3, wherein the curved guide slot defines a slot width measured along a direction perpendicular to the curved slot axis, and the slot width is slightly greater than a major diameter of a shaft of the bone screw.

7. The bone fixation system of claim 3, wherein the curved guide slot extends through the plate body from an upper hole perimeter at an interface with the outer surface of the plate body to a lower hole perimeter at an interface with the bone-facing surface of the plate body, and the curved guide slot includes a countersink extending from the upper hole perimeter toward the lower hole perimeter.

8. The bone fixation system of claim 1, wherein the second plate hole arrangement of the plate body comprises a pair of second holes laterally spaced from each other along an arrangement axis that intersects central axes of the pair of second holes, and the arrangement axis extends across the longitudinal plate axis.

9. The bone fixation system of claim 8, wherein the pair of second holes are variable angle locking (VAL) holes, the at least one second locking member comprises a pair of variable angle locking (VAL) screws configured for variable angle locking with the pair of second holes.

10. The bone fixation system of claim 9, wherein the pair of VAL screws are configured to extend through the VAL holes and into underlying bone alongside opposite lateral sides of the nail body at a location of the nail body distally spaced from the nail hole, and the pair of VAL screws are configured to lock with the plate body for limiting the intramedullary nail from moving laterally relative to the underlying bone.

11. A bone plate configured to attach to an underlying bone, the bone plate comprising:

a plate body having a first end and a second end opposite each other along a longitudinal direction, the plate body defining a longitudinal axis that extends between the first and second ends along the longitudinal direction, the plate body having a first side and a second side opposite each other along a lateral direction offset from the longitudinal direction, the plate body having a bone-facing surface and an outer surface opposite each other along a transverse direction offset from the longitudinal and lateral directions, the plate body defining a first hole and a second hole arrangement each extending from the outer surface to the bone-facing surface, the second hole arrangement spaced distally from the first hole along the longitudinal direction, the first hole configured to receive a first fixation member that is configured to purchase with the underlying bone, the second hole arrangement configured to receive at least one second fixation member that is configured to purchase with the underlying bone, wherein the plate body is configured to pivot along an angulation range about the first fixation member extending through the first hole and into the underlying bone, wherein the second hole arrangement extends laterally across the longitudinal axis, defines the angulation range, and is configured such that the at least one second fixation member is configured to substantially secure the bone plate to the underlying bone at any selected angulation within the angulation range, and wherein the plate body defines a plurality of third holes that are each configured to receive a respective third fixation member that is configured to purchase with the underlying bone, wherein each of the plurality of third holes extend from the outer surface to the bone-facing surface and are spaced distally from the second hole arrangement.

12. The bone plate of claim 11, wherein the angulation range is from about 10 degrees to about 20 degrees.

13. The bone plate of claim 11, wherein the second hole arrangement comprises a single, curved guide slot that extends along a curved slot axis having at least a directional component along the lateral direction, and the curved guide slot is configured to receive the at least one second locking member.

14. The bone plate of claim 13, wherein the curved slot axis has a radius in a range from about 25.0 mm to about 30.0 mm, as measured from a central axis of the first hole, wherein the radius is substantially constant along the curved slot axis, and wherein the first hole is defined by a circumferentially extending surface, of the plate body, that is circumferentially continuous.

15. The bone plate of claim 11, wherein the second hole arrangement comprises a pair of second holes laterally spaced from each other along an arrangement axis that intersects central axes of the pair of second holes, wherein the arrangement axis extends across the longitudinal axis, and the pair of second holes are variable angle locking (VAL) holes configured to receive variable angle locking (VAL) screws.

16. The bone plate of claim 11, further comprising the first fixation member, the at least one second fixation member, and at least one of the third fixation members, wherein the plate body comprises a proximal end and a distal end that is distally spaced from the proximal end, wherein the plurality of third holes are disposed closer to the distal end of the plate body than the proximal end of the plate body, and wherein the first hole and the second hole arrangement are disposed closer to the proximal end of the plate body than the distal end of the plate body.

17. A method for treating a bone, comprising:
inserting an intramedullary nail into a medullary canal of the bone;
placing a bone plate alongside the bone, the bone plate having proximal and distal ends opposite each other along a longitudinal direction;
inserting a first locking member through a first plate hole defined in the bone plate, into an underlying bone, and at least into a nail hole defined in the intramedullary nail, the first plate hole defined in a proximal portion of the bone plate;
pivoting the bone plate about the first locking member until a portion of the bone plate distal of the proximal portion is aligned with a distal portion of the intramedullary nail;
inserting at least one fixation member through at least one fixation hole defined in the portion of the bone plate distal of the proximal portion and into the underlying bone;
inserting at least one second locking member through at least one second plate hole defined in the bone plate and into the underlying bone adjacent the intramedullary nail, advancing the at least one second locking member through the at least one second plate hole such that a head of the at least one second locking member becomes fully seated in the at least one second plate hole, wherein the at least one second plate hole is distally spaced from the first plate hole along the longitudinal direction; and
after the pivoting and aligning step, further advancing the first locking member until a head of the first locking member is fully seated in the first plate hole.

18. The method of claim 17, wherein:
the at least one second plate hole is a single, curved guide slot that extends along a slot axis between opposed lateral ends of the curved guide slot, the slot axis intersects a longitudinal axis of the bone plate, the at least one second locking member is a bone screw, and the step of inserting the at least one second locking member comprises inserting the bone screw through the curved guide slot and into the underlying bone and at least into a second nail hole distally spaced from the nail hole, and
the pivoting step causes longitudinally opposed sides of the curved guide slot to slide alongside longitudinally opposed sides of a shaft of the bone screw, wherein the curved guide slot defines a pivoting angulation range bounded by the opposed lateral ends of the curved guide slot abutting against laterally opposed sides of the shaft of the bone screw.

19. The method of claim 18, wherein the curved guide slot includes a countersink, the bone screw has a screw head having a smooth, untreaded outer surface, and the step of further advancing the first locking member causes the smooth, unthreaded outer surface of the screw head to seat against the countersink and press the bone plate toward the underlying bone.

20. The method of claim 17, wherein:
the at least one second plate hole is a pair of second variable angle locking (VAL) holes spaced from each other along an arrangement axis having at least a directional component along a lateral direction that is substantially perpendicular to the longitudinal direction, and the at least one second locking member is a pair of second variable angle locking (VAL) bone screws, and
the step of inserting the at least one second locking member comprises inserting the pair of second VAL bone screws respective through the pair of second VAL holes and into the underlying bone alongside opposite lateral sides of the intramedullary nail at a location of the intramedullary nail distally spaced from the nail hole.

* * * * *